United States Patent
Jones et al.

(10) Patent No.: US 7,145,571 B2
(45) Date of Patent: *Dec. 5, 2006

(54) TECHNIQUE FOR ENABLING COLOR BLIND PERSONS TO DISTINGUISH BETWEEN VARIOUS COLORS

(75) Inventors: Peter W. J. Jones, Belmont, MA (US); Dennis W. Purcell, Medford, MA (US)

(73) Assignee: Tenebraex Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/388,803

(22) Filed: Mar. 13, 2003

(65) Prior Publication Data

US 2004/0085327 A1 May 6, 2004

Related U.S. Application Data

(60) Provisional application No. 60/422,960, filed on Nov. 1, 2002.

(51) Int. Cl.
G09G 5/02 (2006.01)
(52) U.S. Cl. .............. 345/589; 345/582; 345/592; 345/593; 345/629
(58) Field of Classification Search ............. 345/582, 345/589, 592, 593, 629
See application file for complete search history.

(56) References Cited

U.S. PATENT DOCUMENTS

| | | | |
|---|---|---|---|
| 1,616,604 A | 2/1927 | Brophy | |
| 2,937,567 A | 5/1960 | Hardey et al. | |
| 4,285,580 A | 8/1981 | Murr | |
| 5,467,123 A | 11/1995 | Zeevi et al. | |
| 5,568,596 A * | 10/1996 | Cawley | 345/603 |
| 5,589,898 A | 12/1996 | Atkinson | |
| 5,636,038 A | 6/1997 | Lynt et al. | |
| 5,898,381 A | 4/1999 | Gartner et al. | |
| 5,917,573 A | 6/1999 | Davis et al. | |
| 5,973,663 A * | 10/1999 | Bates et al. | 345/786 |
| 6,052,126 A * | 4/2000 | Sakurababa et al. | 345/582 |
| 6,054,932 A | 4/2000 | Gartner et al. | |
| 6,081,276 A | 6/2000 | Delp et al. | |
| 6,192,341 B1 * | 2/2001 | Becker et al. | 704/271 |
| 6,210,006 B1 | 4/2001 | Menozzi | |
| 6,211,779 B1 | 4/2001 | Gibb et al. | |
| 6,306,459 B1 | 10/2001 | Fleming | |
| 6,340,868 B1 | 1/2002 | Lys et al. | |
| 6,345,128 B1 | 2/2002 | Stokes | |
| 6,461,008 B1 | 10/2002 | Pederson | |
| 6,549,660 B1 * | 4/2003 | Lipson et al. | 382/224 |
| 6,591,008 B1 | 7/2003 | Surve et al. | |
| 6,650,772 B1 * | 11/2003 | Inoue et al. | 382/162 |
| 6,729,729 B1 | 5/2004 | Irons | |
| 6,769,138 B1 | 8/2004 | Golle et al. | |

(Continued)

FOREIGN PATENT DOCUMENTS

DE 4400021 A1 7/1995

(Continued)

Primary Examiner—Kee M. Tung
Assistant Examiner—Mike Rahmjoo
(74) Attorney, Agent, or Firm—Fish & Neave IP Group Ropes & Gray LLP

(57) ABSTRACT

Systems and methods for processing data representative of a full color image. Such systems may comprise the steps of assisting a color blind person to indicate portions of an image which to their color-deficient vision are indistinguishable, and altering the image to cause those portions to become distinguisable and identifiable.

27 Claims, 22 Drawing Sheets

U.S. PATENT DOCUMENTS

| | | |
|---|---|---|
| 6,851,809 B1 | 2/2005 | Sachtler |
| 2002/0075278 A1* | 6/2002 | Kakutani .................... 345/600 |
| 2002/0145805 A1 | 10/2002 | Hall |
| 2003/0053094 A1* | 3/2003 | Ohga et al. .................. 358/1.9 |
| 2003/0095705 A1 | 5/2003 | Weast |
| 2004/0056965 A1 | 3/2004 | Bevans et al. |
| 2004/0085327 A1 | 5/2004 | Jones et al. |
| 2004/0212815 A1 | 10/2004 | Heeman et al. |
| 2005/0152141 A1 | 7/2005 | Traynor |

FOREIGN PATENT DOCUMENTS

| | | |
|---|---|---|
| JP | 10003596 | 1/1998 |
| JP | 11-184532 | 1/2001 |

* cited by examiner

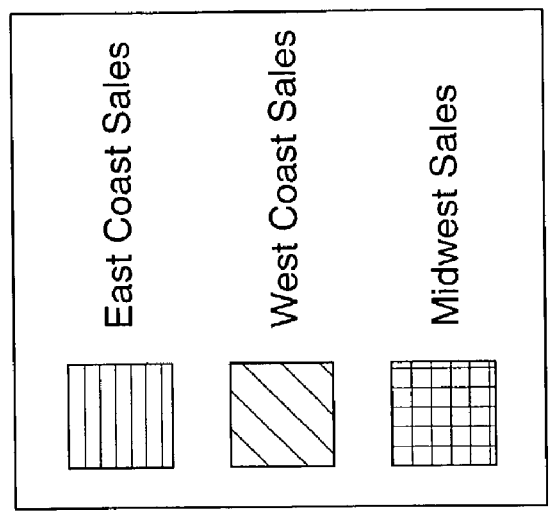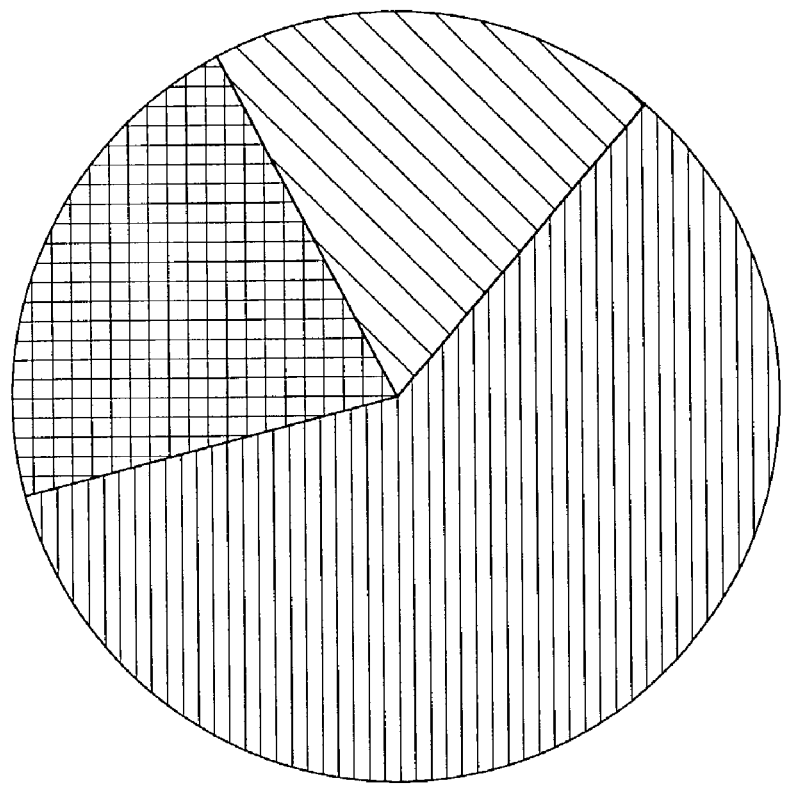
Fig 10

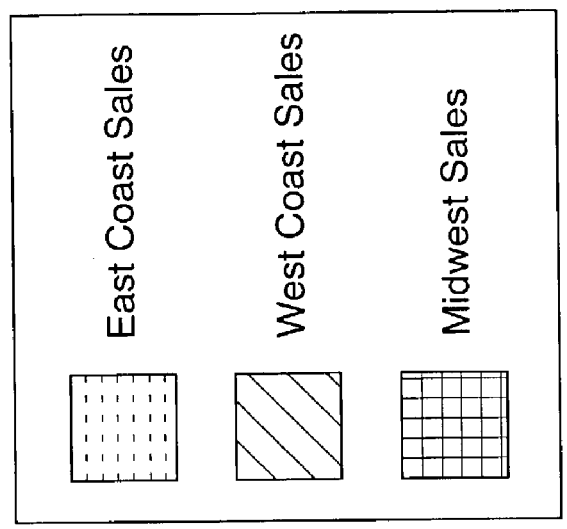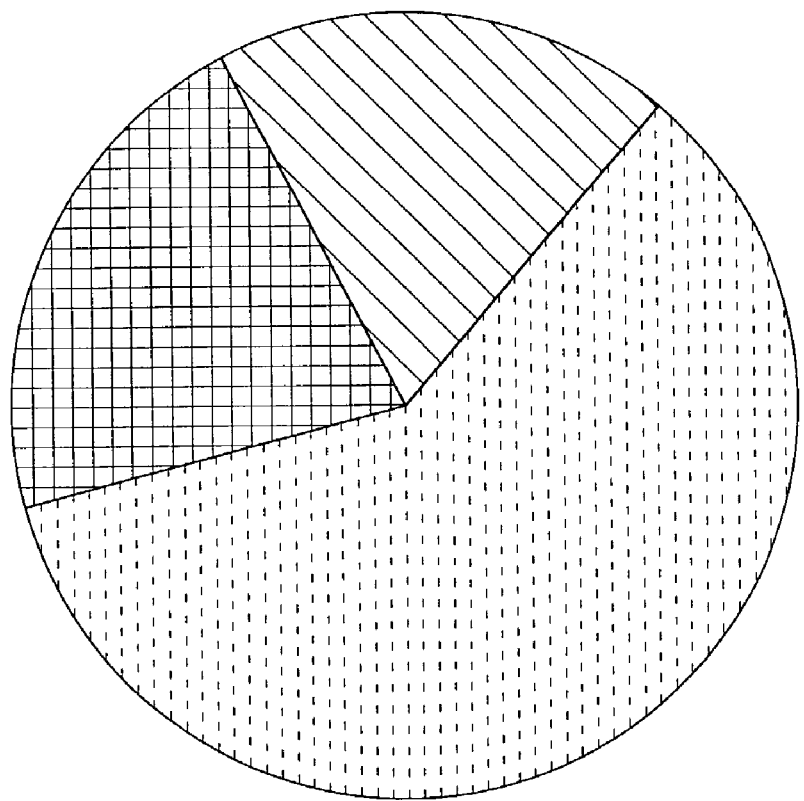
Fig 11

TECHNIQUE FOR ENABLING COLOR BLIND PERSONS TO DISTINGUISH BETWEEN VARIOUS COLORS

REFERENCE TO RELATED APPLICATIONS

This application claims priority to U.S. Ser. No. 60/422,960 filed Nov. 1, 2002, entitled Technique For Enabling Color Blind Persons To Distinguish Between Various Colors, and naming Peter Jones and Dennis Purcell as inventors, the contents of which are hereby incorporated by reference.

BACKGROUND OF THE INVENTION

Color-blind persons have difficulty distinguishing various colors. Persons whose color vision is impaired include, for example, those who confuse reds and greens (e.g., either protanopia: having defective red cones or deuteranopia: having defective green cones). Jennifer Birch, Diagnosis of Defective Color Vision, Butterworth Heinman (2002). For these people visual discrimination of color-coded data is practically impossible when green, red or yellow data is adjacent. In the color space of such persons, the red-green hue dimension is missing, and red and green are both seen as yellow; they have only the yellow-blue dimension. Even people with normal color vision can, at times, have difficulty distinguishing between colors. As for elderly persons, as a person ages clouding of the lenses of their eyes tends to occur, due, for example, to cataracts. The elderly often experience changes in their ability to sense colors, and many see objects as if they have been viewed through yellowish filters. Additionally, over time ultraviolet rays degenerate proteins in the eye, and light having short wavelengths is absorbed and blue cone sensitivity is thereby reduced. As a result, the appearance of all colors changes, yellow tending to predominate, or a blue or a bluish violet color tends to become darker. Specifically, "white and yellow," "blue and black" and "green and blue" are difficult to distinguish. Similarly, even a healthy individual with "normal" vision can perceive colors differently when they are at an altitude that is greater than they are normally used to, or under certain medications.

To overcome the inability to distinguish colors, such individuals become adept at identifying and learning reliable cues that indicate the color of an object, such as by knowing that a stop sign is red or that a banana is typically yellow. However, absent these cues, the effect of being color-blind is that they are often unable to reliably distinguish colors of various objects and images, including in cases where the color provides information that is important or even critical to an accurate interpretation of the object or image. Common examples of such objects and images include lighted and non-lighted traffic signals, and pie-charts/graphs of financial information and maps. Moreover, with the proliferation of color computer displays, more and more information is being delivered electronically and visually and usually with color coded information.

To address the fact that important information may be color coded, engineers and scientists have developed a number of devices to aid a color-blind person. For example, U.S. Pat. No. 4,300,819 describes eyeglasses for distinguishing colors using one colored and one clear lens. Similarly, U.S. Pat. No. 4,998,817 describes a corneal contact lens for distinguishing of colors, which is clear except for a thin red exterior layer covering the area admitting light to the pupil.

Although such devices provide some benefit, they are cumbersome to use and have limited effectiveness in that only one color is adjusted, and the user cannot expand or change the manner in which the device alters the perceived color space.

Thus, a user viewing a pie chart that includes a plurality of colors that are outside of the perceptible color space of his or her vision, will have only a moderately improved understanding of the information being conveyed in the pie chart. Therefore, a great load is imposed on such persons when they must read or edit data using a color computer display terminal. In addition, these users cannot locate information on a screen that is displayed using certain colors or color combinations, and thus might not be able to read important notices. For example, when such a user employs a service or resource provided via the Internet, such as an electronic business transaction, or an on-line presentation, it may be that important information or cautionary notes are displayed using characters in colors that the individual may not be able to distinguish.

Accordingly, there is a need for improved systems for aiding in the identification of colors and color-coded information.

SUMMARY OF THE INVENTION

The systems and methods described herein enable a user to more easily distinguish or identify information that has been color-coded within an image. Although the systems and methods described herein will be discussed with reference to systems and applications adapted to aid a color blind user, it will be understood that these systems and methods may be employed to help any individual distinguish or understand color coded information. In general, color blind persons have difficulty in differentiating between two or more colors. For instance, a red/green color blind person may have difficulty in interpreting the signals of traffic lights or marine navigation aides. Also, mixed colors such as brown (green+red), magenta (red+blue) and cyan (green+blue) can be difficult to distinguish. Accordingly, it is an advantage of this technique to permit color blind persons to distinguish various colors or color-coded information, such as red information from green information.

In one aspect, the systems and methods described herein include methods for processing data representative of a full color image, comprising the steps of identifying a color space associated with the data, identifying a first portion of the color space being indistinguishable to color blind individuals, processing the data to identify a second portion of the color space that is perceptible to color blind individuals, and processing the first portion of the color space as a function of colors in the second portion of the color space.

This technique re-maps color information from one portion of the color-space to another portion. Alternately, this technique can remap color information onto a dimension that is not color based, such as time (e.g. flashing or blinking) or texture (e.g. hatching). In alternate embodiments, the systems and methods described herein may be realized as software devices, such as device drivers, video drivers, application programs, and macros, that modify the normal output of a computer program to provide information that a color blind person can employ to identify or distinguish those sections of the display that are being presented in colors normally outside the color range of that person.

BRIEF DESCRIPTION OF THE DRAWINGS

The foregoing and other objects and advantages of the invention will be appreciated more fully from the following further description thereof, with reference to the accompanying drawings wherein;

FIGS. 10 and 11 depict an alternative process and method for encoding color information into a format detectable by a color blind user.

DESCRIPTION OF THE ILLUSTRATED EMBODIMENTS

Figure 1:
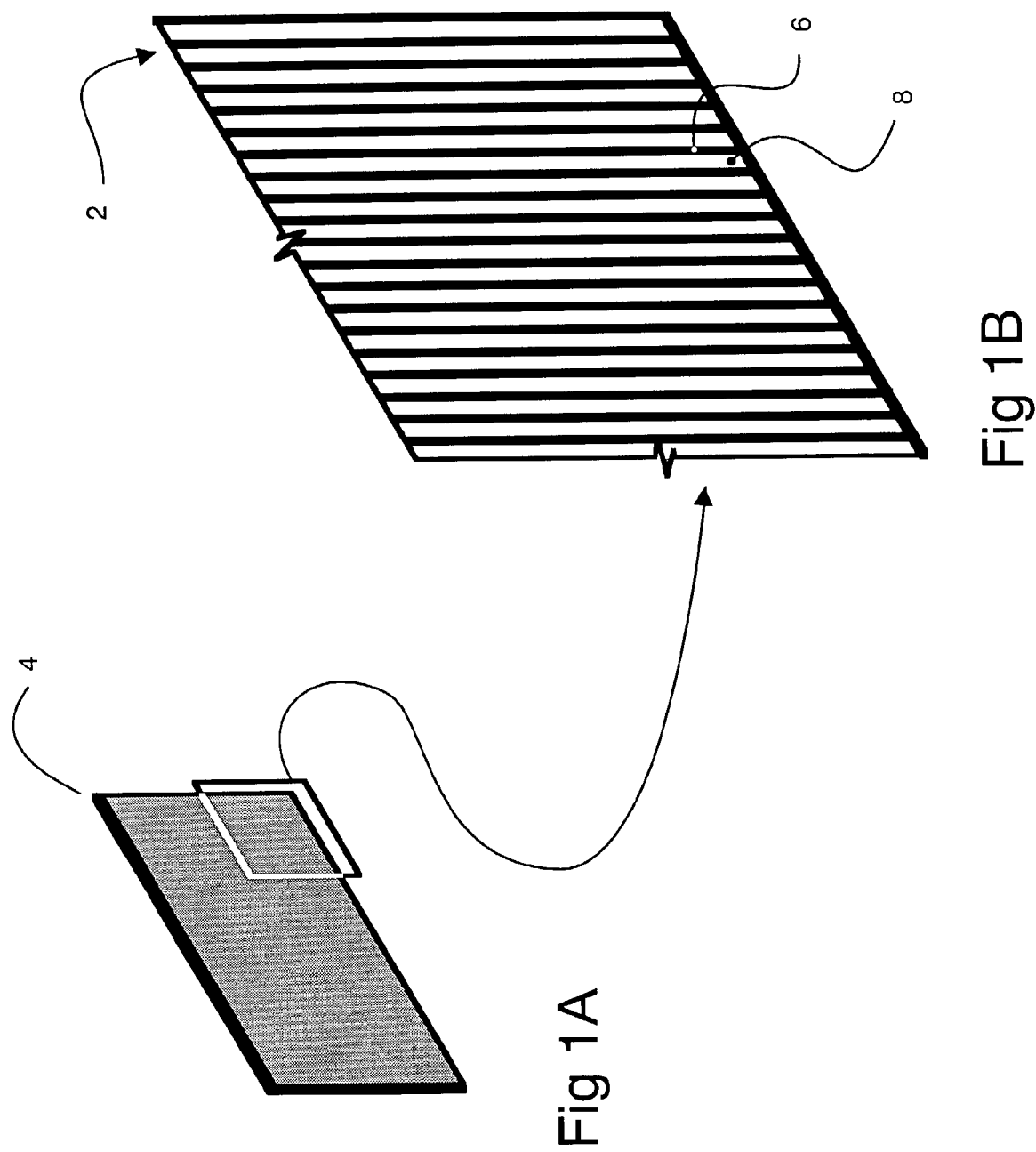
FIGS. 1A and 1B are illustrations depicting a filter panel comprised of a pattern of transparent minus-red electronic filter elements.

To provide an overall understanding of the invention, certain illustrative embodiments will now be described. However, it will be understood by one of ordinary skill in the art that the systems and methods described herein can be adapted and modified for other suitable applications and that such other additions and modifications will not depart from the scope hereof.

In one embodiment, the techniques and inventions described herein enable a color blind person, as well as a person with normal color vision, to distinguish various colors by employing a device that creates an intermittent blinking pattern, and, thus, serves an additional channel of information. More specifically, the systems and methods described herein include apparatus and processes that code color information that is indistinguishable by a color blind individual onto a channel of information that is detectable by the individual. In one embodiment, the systems and methods described herein include software programs that analyze and modify color information associated with a display. As described in more detail below, these programs can, in one practice, identify or receive user input representative of the type of color blindness to address. For example, the user may indicate that they have red-green color blindness. In response to this input, the process may review, on a pixel-by-pixel basis, color information associated with an image being displayed. The process may determine the difference between the red and green color components, and thereby make a determination of the color information being displayed that is not detectable by the user. The process may then encode this color information in an alternate, optionally user-selectable way. For example, the user may chose to have the red or green components fade to white or darken to black. The rate at or extent to which colors fade or darken may vary according to user input the color information that was being presented. In this way, the user can see that portions of the image are fading in and out, indicating that these portions of the image carry color information that is otherwise indistinguishable. In this way, red or green portions of a display—such as red and green items on a map or navigation chart can be distinguished by the user.

The systems and methods described herein aid color-vision impaired individuals by processing color-coded information that is not perceptible to these individuals and recoding the information onto a channel that is perceptible to the individuals, such as by recoding the color information onto a visually perceptible temporal pattern that is detectable by all sighted people. To this end, these systems recode color coded information to allow color vision impaired people to differentiate between two colors, typically red and green.

The systems and methods described herein provide alternate ways to visually present information, and in particular color information to a user. These systems have wide applicability, including for providing systems that make it more easy for a user to distinguish color coded information presented in a pie chart, a graph, a map or in some other format. Additionally, these systems can process color information in a manner that presents the information in a format that can be perceived by a person with impaired color-vision. To this end, the systems and method described herein, inter alai, provide a user with control over the color palette and hues being used to display information. By controlling the color, a user can redirect color coded information into a format that is more easily perceived by the user.

Interposing Filters (Temporal Encoding)

In one embodiment, the systems and methods disclosed herein interpose a filter between the user and the color coded information for the purpose of temporally encoding the color data. The system intermittently interposes a filter that blocks a certain color of light in front of a color blind person's eyes. For instance, FIGS. 1A and 1B show a filter panel 4 and a close-up of the filter panel 4. In this embodiment the filter panel 4 is made up of a pattern of transparent minus-red electronic filter elements 6 laid down on a transparent field 8. The pattern comprises vertical stripes of clear plastic and stripes of minus-red filter elements 16. Such filter elements 16 are commercially available, including LCD minus-red filters used in the color changing sun glasses manufactured and sold by Reliant technology company of Foster City California and described is detail in U.S. Pat. No. 5,114,218, the contents of which are incorporated by reference. Such filters 16 may be integrated into the panel 4 as described in the referenced patent, so that the panel is formed as an LCD plate with the LCD minus-red filters 16 formed as a pattern of stripes integrated into the plate 4. Alternatively, the panel 4 may include minus-green filters or a filter of another selected color, and filter chosen will depend, at least in part on the application at hand. Similarly, the pattern may comprise vertical stripes, horizontal stripes, a checker board pattern or any other suitable pattern. These filter elements are switched on and off periodically so as to let red light pass through the panel one moment and block red light from passing through the next moment.

Figure 2:
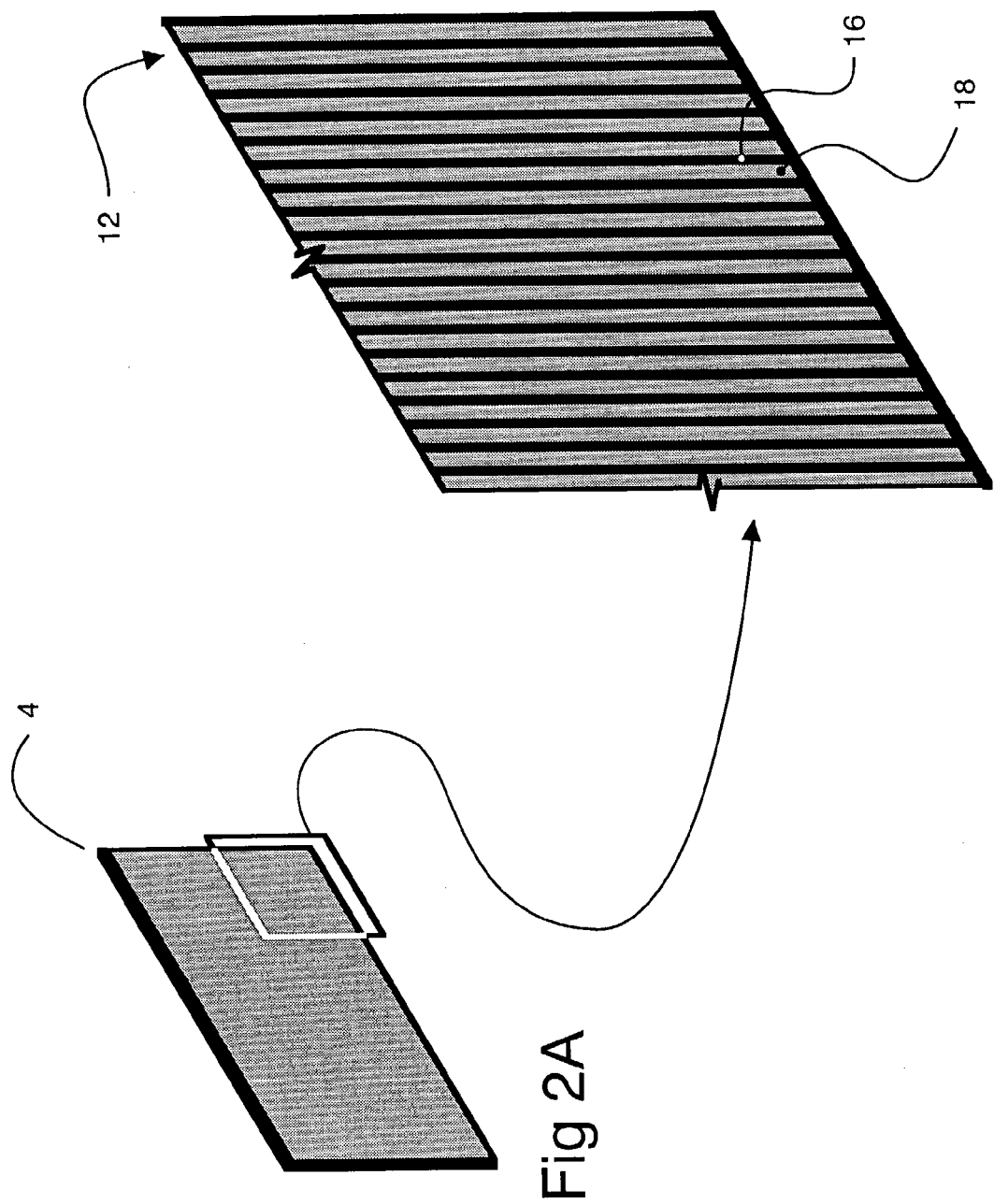
FIGS. 2A and 2B are illustrations depicting a filter panel comprised of a pattern of transparent minus-red electronic filter elements alternating with transparent neutral density electronic filter elements.

FIGS. 2A and 2B depict another filter panel 14 and its close-up 12. Through a combination of filter elements 16 and 18, this filter panel 14 minimizes the impression of flickering. Moreover, the filter panel 14 in FIG. 2B is comprised of a pattern of transparent minus-red electronic filters 16, alternating with transparent neutral density electronic filters 18. The neutral density filters may be any suitable neutral density filter. In one embodiment the neutral density filter includes a filter similar to the color filters described in the above referenced patent. However, rather than colors, the filter may provide for different levels of grey to allow for different density filters. The minus-red and neutral density filter elements 16 and 18 are turned on and off in an alternating fashion so that when the minus-red filter element 16 is on and blocking red light, the neutral density filter is off and passing light. Conversely, when the minus-red filter 16 is turned off and passing red light, the neutral density filter 18 is turned on and blocking a selected percentage of light. Accordingly, the impression of flickering is reduced or minimized when the minus-red filter 16 is switched on and off.

The filter panel 14 depicted in FIG. 2A as well as the filter panel 4 depicted in FIG. 1A can operate under microprocessor control. To this end, a microprocessor or a microcontroller may be employed for generating an electronic timing control circuit that can turn the filters 16 and 18 on and off in an alternating fashion and according to a period or frequency that is suitable for the application. Additionally, and optionally, the electronic filters 16 and 18 may be tunable for selecting the color or range of colors to be filtered. These microcontrollers can be developed using principles well known in the art. In further optional embodiments, the system can include a sensor that determines the lighting level of the relevant environment. Such optical sensors are known in the art and any suitable sensor that can measure the brightness of the environment may be employed. The brightness level may be used by the microcontroller to balance the amount of neutral density used by the system as a function of the brightness of the environment.

Figure 3:
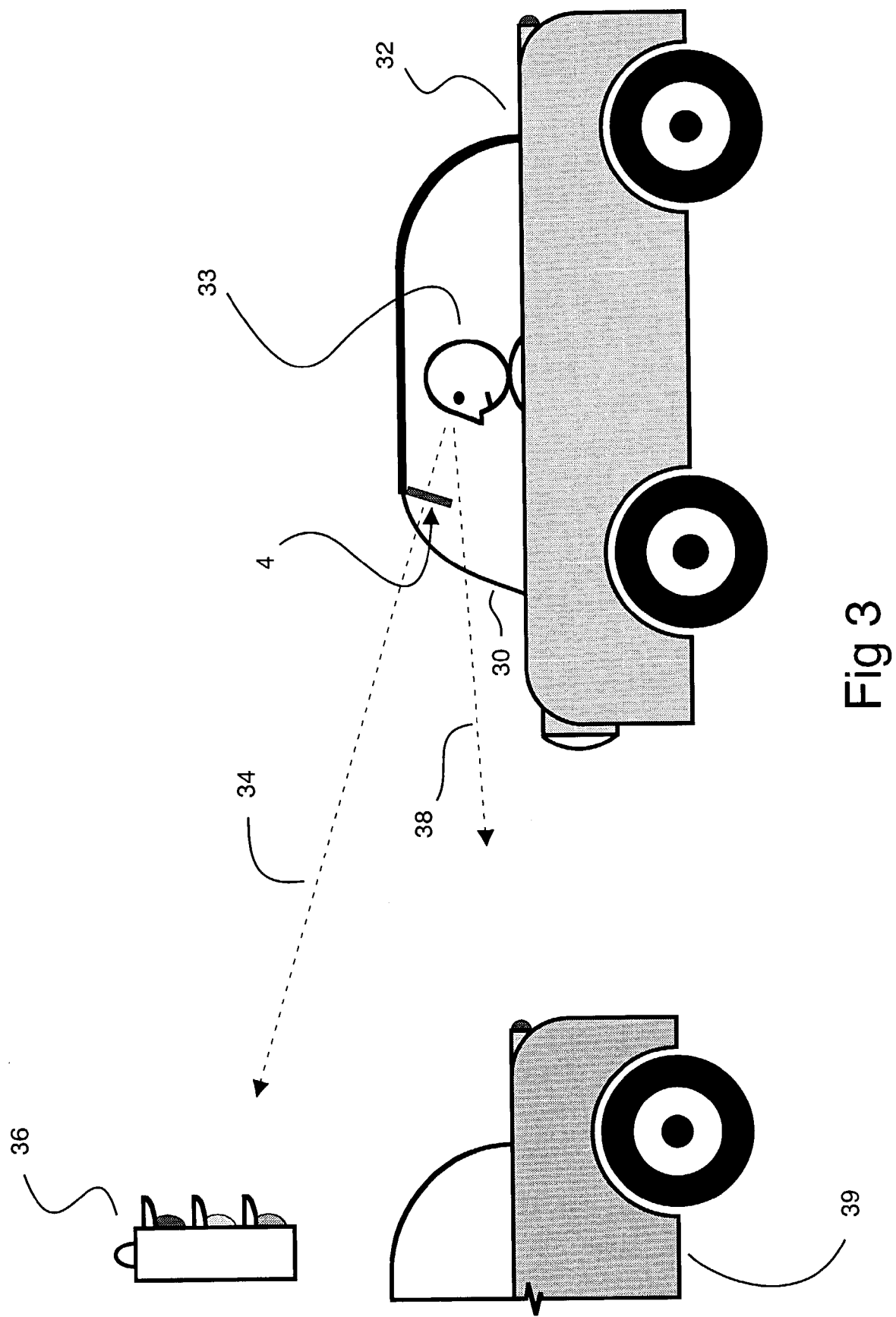
FIG. 3 is an illustration depicting a possible application of the invention mounted as an adjustable visor to aid the driver in interpreting traffic signals.

In alternate embodiments, a mechanical intermittent filter is provided. For example, in one such alternate embodiment, a mechanical filter comprises a plurality of rotatable filter elements disposed across the surface of a clear plate. Each filter can comprise a thin sheet of acetate that acts as a minus-red filter. The filter can be rotated in and out of the view of the user. To this end, each filter may be mounted on an axle and may be driven by a servo-motor. The servo motor can operate under the control of a micro controller. The filter may be mounted as shown in FIG. 3 to allow a user 33 to view traffic signals 36 through the filter. The user 33 has a straight line of sight 38 and a line of sight 34 that is inclined and travels through the visor panel 4 to the signal 36.

In operation, the user 33 moves the filter 4 or 14 into position just as a sun visor may be moved into position. The user 33 activates the filter 4 so that the filter 16 and 18 begin to intermittently filter out a selected color of light, such as red light. The result is that a red light viewed through the filter 4 appears to flash. Thus, the user 33 can distinguish between a red light or green light at the traffic signal 36. In this way, the filter 4 remaps the color information provided by traffic signal 36 into a temporal pattern that the user 33, even if red-green color blind can detect.

The technique of interposing an intermittent filter panel can be employed in numerous devices. Although, FIG. 3 depicts the use of an intermittent filter panel in an overhead visor to aid a driver 33 in distinguishing a red traffic signal 36 from a green signal 36 the filter can be used in numerous other applications including, marine navigation, air transport, and others. Additionally, other types of optical filters may be used including mechanical filter devices that rotate the filters in and out of the user's 33 line of sight, or can slide filters across the field of view so that the filters vibrate over the panel 4. Additionally, in certain optional embodiments, the filters can be formed in a pattern of tight stripes. For example, strips of red or green acetate placed of the surface of the panel. The panel 4 may be mounted on the vehicle 32 by a spring that allows the panel to vibrate as the vehicle 36 moves. The filters may be fixed is place on the panel, yet the movement of the panel 4 in a motion that is transverse to the user's 33 line of sight, effectively causes the filter to intermittently move across the user's 33 filed of view, thereby causing a traffic light 36 of the selected color to flash.

Coding Color Information into an Alternate Channel

Figure 4:
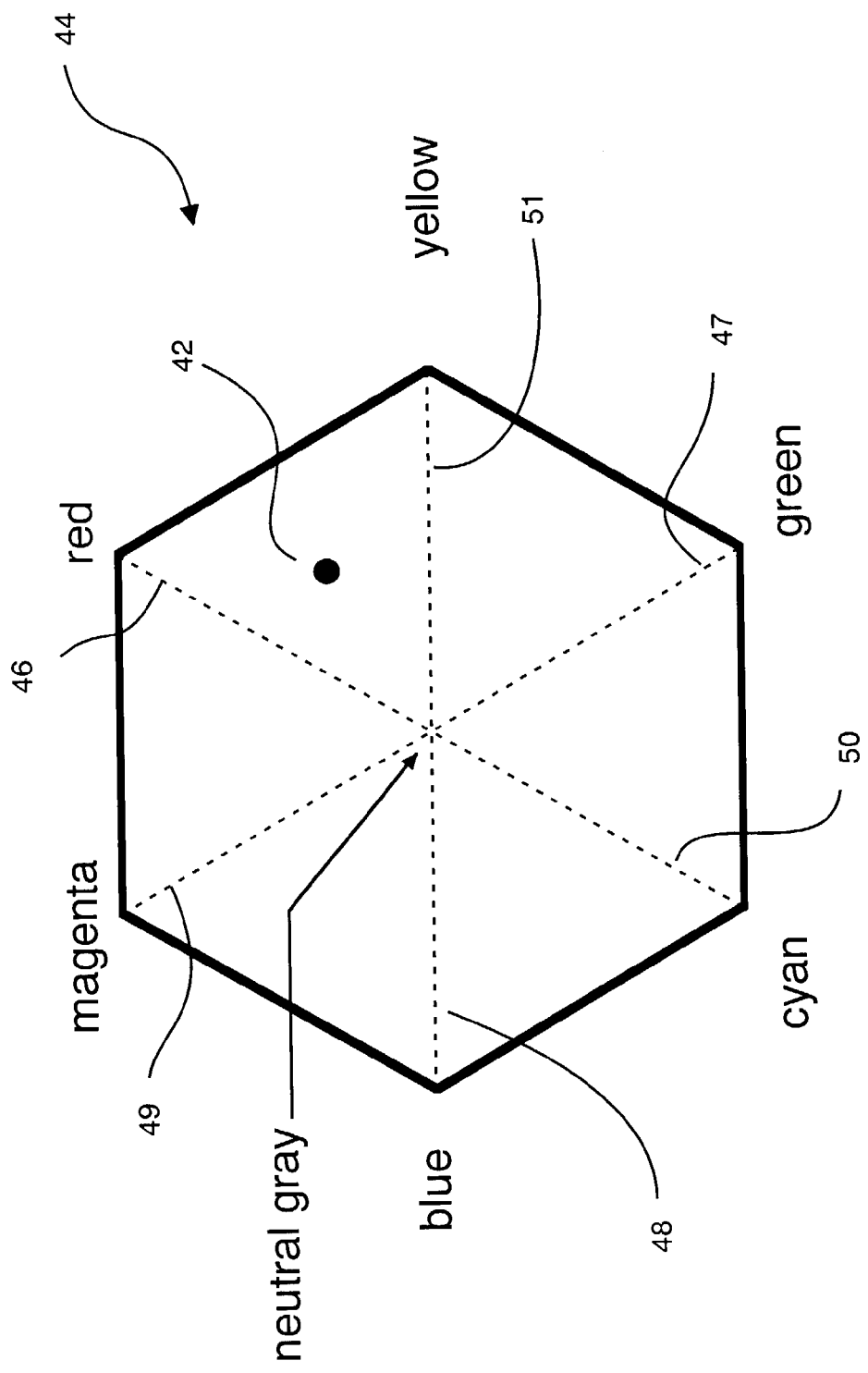
FIGS. 4–6 depict color charts and a process for coding information on that color chart into an alternate display channel.

FIG. 4 depicts a slice 44 through a cube that represents a three dimensional color space. The color space can be any color space and it will be understood to represents all the possible colors that can be produced by an output device, such as a monitor, color printer, photographic film or printing press, or that appear in an image. The definition of various color spaces are known to those of skill in the art, and the systems and methods described herein may be employed with any of these defined color spaces, with the actual definition selected depending at least in part on the application. These models include the RGB color space model, which uses the three primary colors of transmitted light. The RGB standard is an additive color model as if you add red, green and blue light and you get white. A second known color space model uses reflected light. This subtractive color model attains white by subtracting pigments that reflect cyan, magenta and yellow (CMY) light. Printing processes, the main subtractive users, add black to create the CMYK color space. Aside from RGB and CMYK, there are other alternative color spaces; here are some of the more common:

INDEXED uses 256 colors. By limiting the palette of colors, indexed color can reduce file size while maintaining visual quality.

LAB COLOR (a.k.a. L*a*b and CIELAB) has a lightness component (L) that ranges from 0 to 100, a green to red range from +120 to −120 and a blue to yellow range from +120 to −120. LAB is used by such software as Photoshop as a intermediary step when converting from one color space to another. LAB is based on the discovery that somewhere between the optical nerve and the brain, retinal color stimuli are translated into distinctions between light and dark, red and green, and blue and yellow.

HSL a spherical color space in which L is the axis of lightness, H is the hue (the angle of a vector in a circular hue plan through the sphere), and S is the saturation (purity of the color, represented by the distance from the center along the hue vector).

MULTICHANNEL uses 256 levels of gray in each channel. A single Multichannel image can contain multiple color modes—e.g. CMYK colors and several spot colors—at the same time.

MONITOR RGB is the color space that reflects the current color profile of a computer monitor.

sRGB is an RGB color space developed by Microsoft and Hewlett-Packard that attempts to create a single, international RGB color space standard for television, print, and digital technologies.

ADOBE RGB contains an extended gamut to make conversion to CMYK more accurate.

YUV (aka Y'CbCr) is the standard for color television and video, where the image is split into luminance (i.e. brightness, represented by Y), and two color difference channels (i.e. blue and red, represented by U and V). The color space for televisions and computer monitors is inherently different and often causes problems with color calibration.

PANTONE is a color matching system maintained by Pantone, Inc.

When discussing color theory in general, particularly as it applies to digital technologies, there are several other important concepts:

HUE—The color reflected from, or transmitted through, an object. In common use, hue refers to the name of the color such as red, orange, or green. Hue is independent of saturation and lightness.

SATURATION (referred to as CHROMINANCE when discussing video)—The strength or purity of a color. Saturation represents the amount of gray in proportion to the hue, measured as a percentage from 0% (gray) to 100% (fully saturated).

LIGHTNESS—Lightness represents the brightness of a color from black to white measured on a scale of 1 to 100.

LOOK-UP TABLE—A look-up table is the mathematical formula or a store of data which controls the adjustment of lightness, saturation hue in a color image or images, and conversion factor for converting between color spaces.

Turning back to FIG. 4, there is depicted a slice 44 through a cube that represents a the R,G, B color space model. This is a representation of the color space known to those of skill in the art. The slice 44 represents a color space in which a plurality of colors can be defined. As shown in FIG. 4, six axes extend from the center point of the slice 44. Three of these axes are labeled red 46, green 47 and blue 48 respectively. The other three are labeled magenta 49, cyan 50 and yellow 51. Neutral is in the center of the color space. A specific color 42 exists in the color space 44, and is disposed about midway between the red 46 and yellow axes 51. This shows the relative amount of each color axis in the specific color 42. Thus, each point in the slice 44 represents a color that can be defined with reference to the depicted axes.

Figure 5:
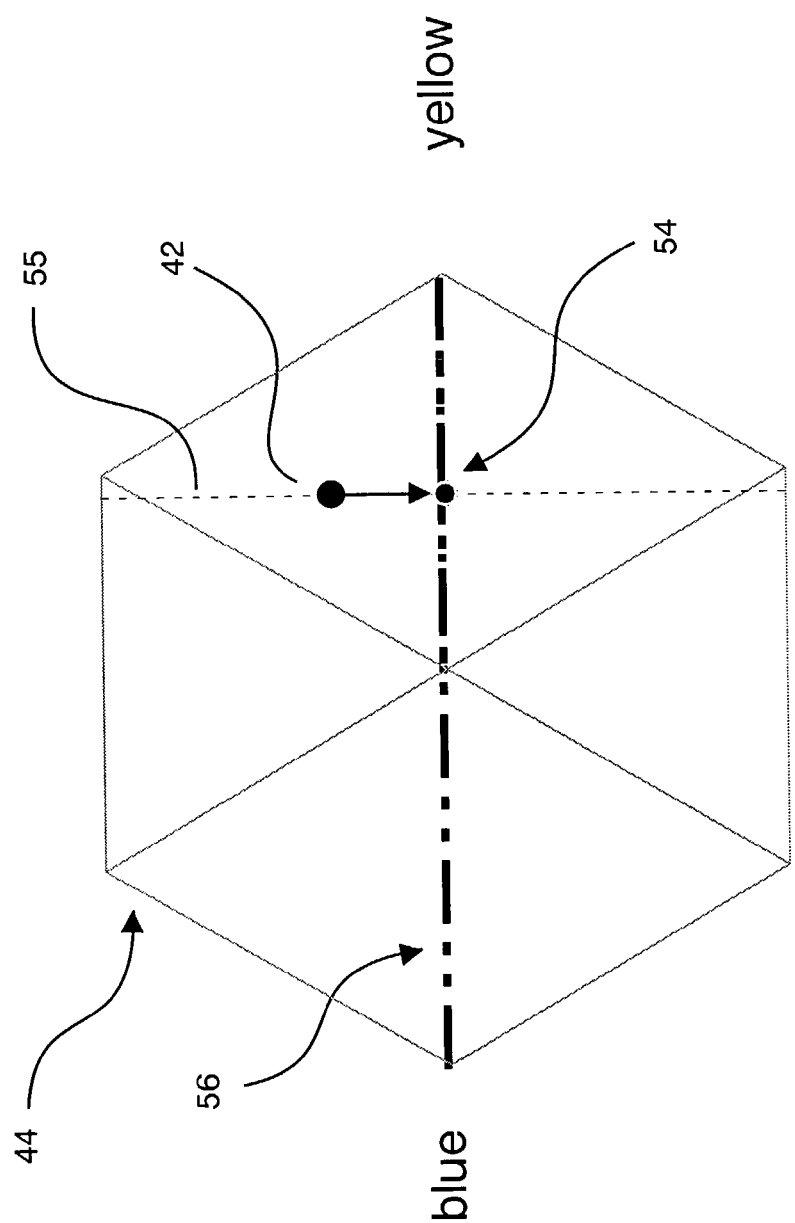

FIG. 5 depicts the color space 44 as seen by a person with red/green color blindness. As a color vision impaired person having red-green color blindness cannot distinguish red or green, the color space perceived by such a person is compressed or reduced. To such a person, all colors, such as the specific color 42, are defined only by their position 54 along the blue-yellow axis 56. Thus, the red component of color 42 is not differentiated by the person and only the component along the blue-yellow axis is differentiated. Thus, this person cannot distinguish between the color 42 and the color 54 that sits on the blue-yellow axis. As such, any information that has been color coded using the color 42 will be indistinguishable from any information that has been color coded using the color 54, or any other color that falls on line 55.

Figure 6:
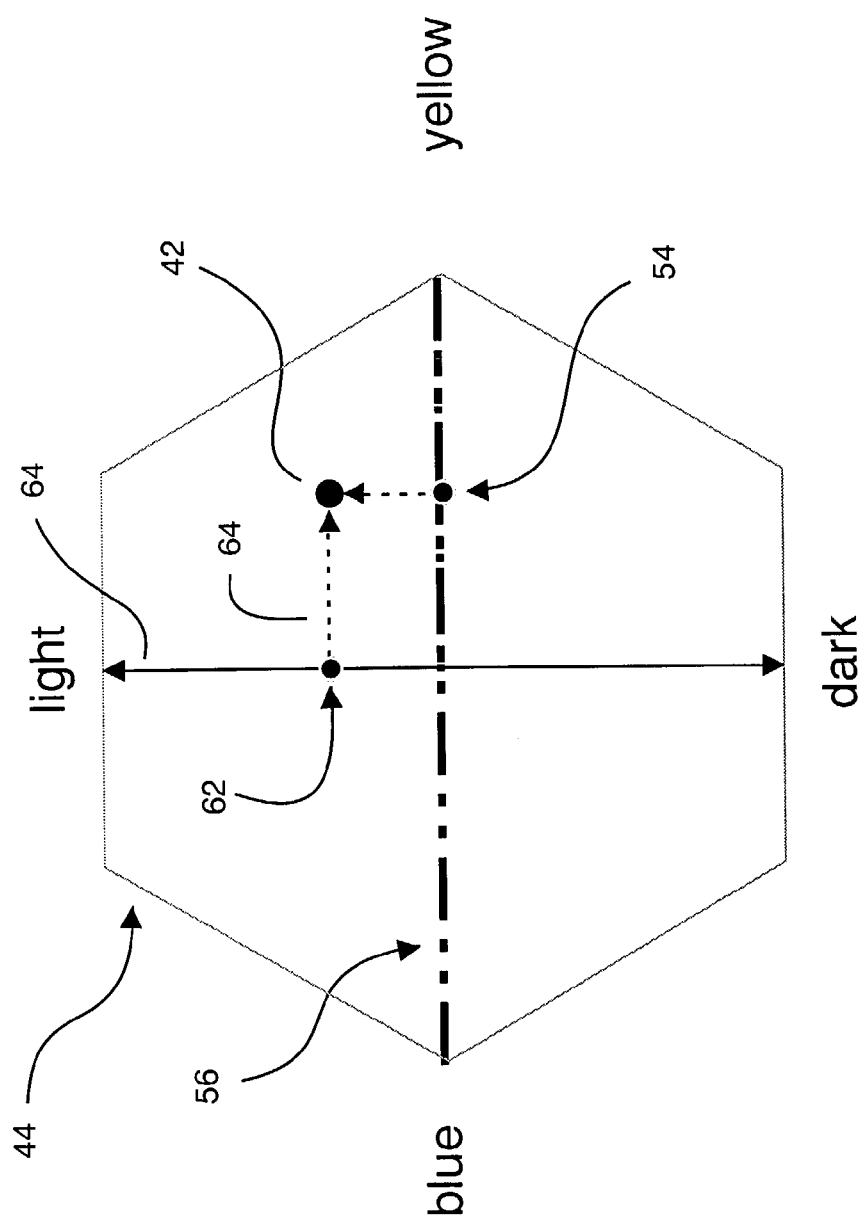

To address this, the systems and methods described herein, in one embodiment, allow a user to distinguish between colors along the line 55 by adding a temporal characteristic related to the color information being displayed. FIG. 6 depicts a method in accordance with this one practice of the invention where the red or green value of the specific color 42 is determined and converted into a selected value 62 on an axis 64 running from light to dark. To this end, and as discussed above, the color map and color 42 is now shown in relation to the axis 64, which represents different degrees of lightness and darkness and which is common in the LAB color space, that also employs a blue-yellow axis. The computer display is then instructed to intermittently change the lightness/darkness value of the specific color 42 to the new value 62, which is lighter or darker depending on the red or green value of the specific color 42. The two values, 62—which is represented temporally by means of a change in lightness/darkness—and 54 are sufficient to locate the actual hue of specific color 42 in a standard color space 44, even though the red/green color blind person has intrinsically only one axis of color perception that lies on the blue-yellow axis 56. Note that in this method, any color that does not have a red or green bias, such as blue or a neutral color, for example, will not have its lightness/darkness intermittently changed. Moreover, note that in one embodiment, the user selects colors having a red component or colors having a green component. In this way, the user can more easily distinguish between reds and greens. Optionally however, the user can have both the red and green color components translated into a degree of lightness/darkness at the same time. The display can lighten flash green-based colors at a rate that is much higher than red-based colors, or can lighten the red-based colors while darkening green-based colors. Either way the systems and methods described herein can recode the green and red hue component of the color 42 onto a temporal variation channel that can be perceived by the user.

Figure 7:
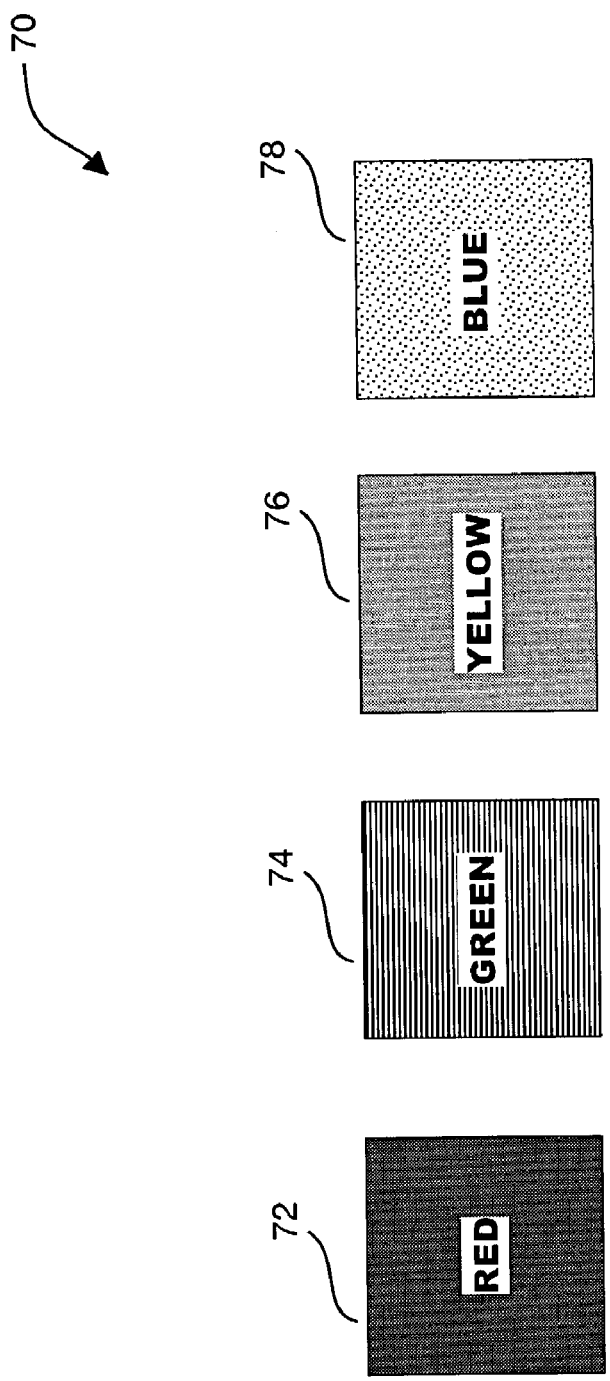
FIGS. 7–9 illustrate a process for encoding color information into a format detectable by a color blind user.
Figure 8:
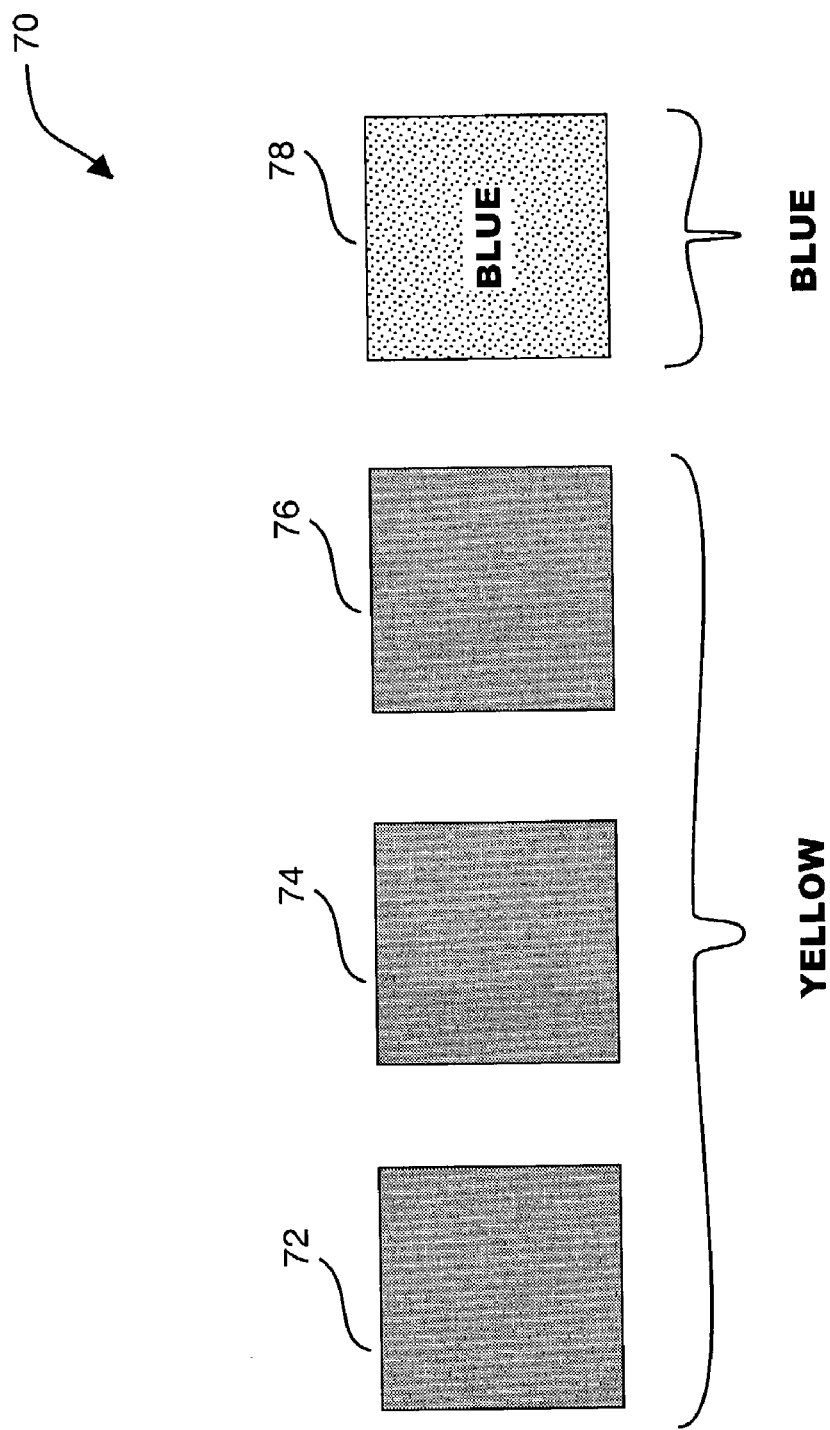
Figure 9:
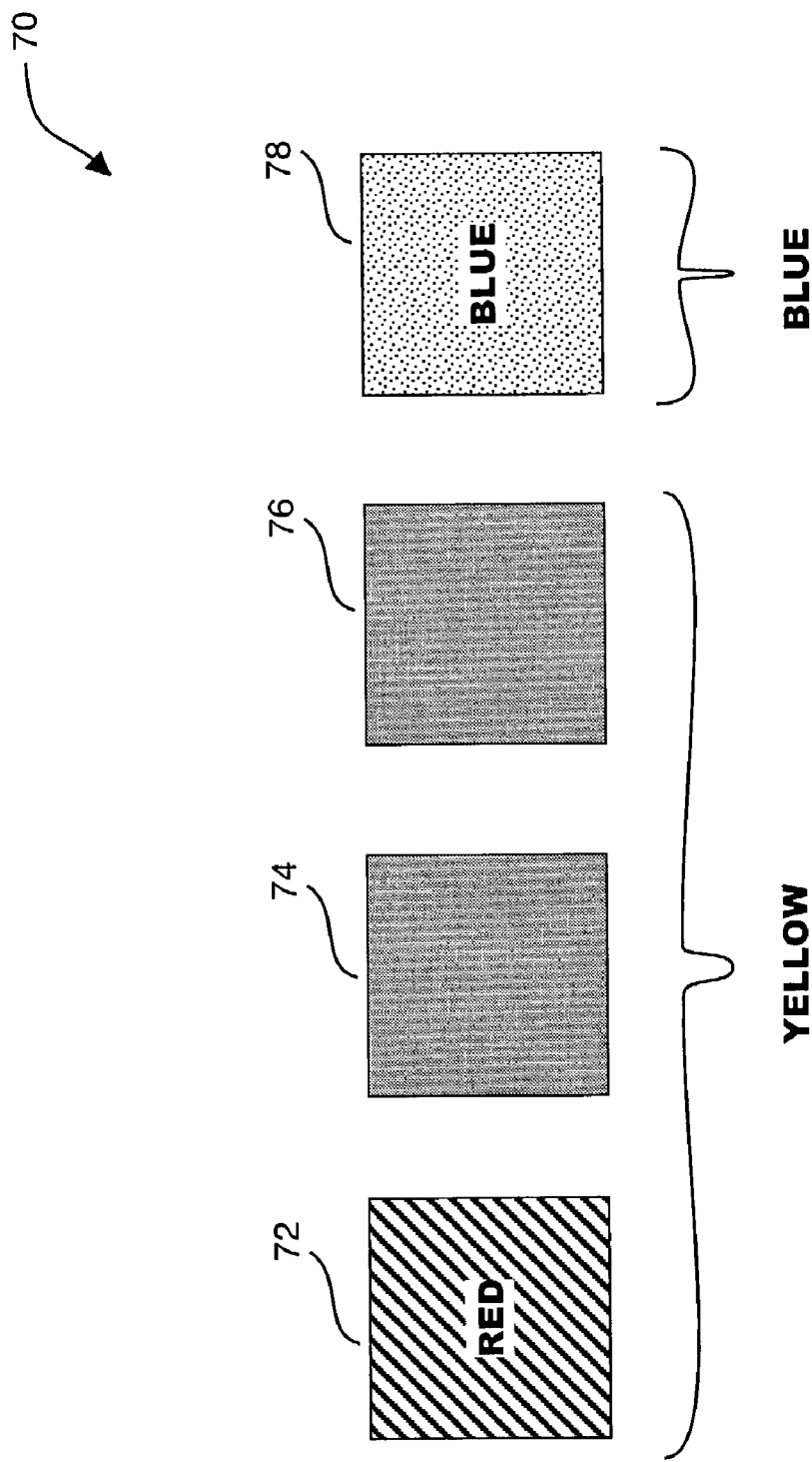

FIGS. 7–9 depict pictorially how the process depicted in FIGS. 4–6 may appear to the user wherein a full-color scene is presented in an alternate format wherein selected colors are encoded into a temporal pattern of alternating dark and light images. In one practice the FIGS. 7–9 represent a display, such as a computer display, that creates a color image. Specifically, FIG. 7 depicts a series of blocks 70 that include a red block 72, a green block 74, and yellow block 76 and a blue block 78. These blocks 70 represent a full-color scene of the type depicted on a computer display.

In FIG. 8 the scene is displayed using only blue-yellow colors, and simulating a red/green color blind person's perception. To this end, the series of blocks 70 are labeled to show that the first three blocks, including the green, red and yellow block all appear yellow to the color-blind user. Thus a display of color coded information that uses reds and greens will fail to convey to the color blind user information that can be used to distinguish between different blocks in the series 70. Thus, if information in red was meant to depict information of high priority, or for example that a stock price was going down, and information in green was meant to convey information of lower or normal priority or a stock price going up, the red-green color blind user would not be able to distinguish this information.

FIG. 9 illustrates that with the application of the systems and methods described herein a user can distinguish between red and green color-coded information. As shown in FIG. 9, the system described herein processes the red-based color components as described above so that red-colors are caused to "flash", optionally at a rate that relates to the amount of red in the color. In this way the user can distinguish the high priority information, which is caused to flash, from the lower priority information, which does not flash. The systems described herein can allow the user, as discussed above, to select at different times, whether to process the red or the green components. Thus, in the embodiment of FIG. 9, the user can choose to process red colors first to determine high priority information and then subsequently process the green colors.

With this practice the systems and methods described herein may be realized as a device or video driver that processes the pixel information in the image to create a new image that more fully conveys to a color-blind person the information in the image. The software may be built into the application program that is creating the image, it may be user controllable so that the user can control the activation of the image processing as well as characteristics of how the image is processed. For example, the invention may provide a "hot-key" that the user can use to activate the process when desired.

Optionally, the invention may provide for mouse "rollover" control wherein moving a cursor over a portion of the screen causes the image, or a color or shape, displayed on that portion of the screen to change at that location and/or at other locations of the display. For example, an image of a graph presented in different colors may be altered by moving the mouse over different portions of the graph to cause the image to change in a manner that communicates to a colorblind person the color-coded information being displayed. To this end, the image may change so that the portion under the cursor and matching colors elsewhere in the image are presented in a textured format, caused to flash, or in some other way altered so that the information being provided by the color of the display is presented in a manner that may be detected by a color blind person.

Texture Mapping

Turning to FIG. 10 an alternative embodiment is depicted. Specifically FIG. 10 depicts a display wherein in a pie chart is presented to a user. To the right of the pie chart is a key table that equates different colors on the graph to different kinds of information. In FIG. 10, solely for purpose of illustration, the colors are represented by different hatch patterns. In FIG. 10 the key table associates colors (depicted by hatch patterns) with different regions of the country. In this embodiment, the user is capable of rolling the cursor over the different colors presented in the key table. This causes the corresponding portion of the pie chart to alter in a manner that may be detected by a color blind person. For example, in FIG. 11, the user may place the cursor over the color used in the Key Table to describe "East Coast" sales. By doing this the system knows to flash or otherwise alter those portions of the pie chart that are presented in that color. Alternatively, the user can place the cursor over a portion of the pie chart and the color in the Key Table associated with that color can flash. Optionally, both functions may be simultaneously supported.

Alternatively, when colored data in an image is known to have certain color names, for example, when a map of highway congestion is known to mark congested zones as red and uncongested zones as green, the colorblind person will be able to select a desired color name from an on-screen list of color names, and colors in the image corresponding to that name will flash or be otherwise identified.

Although, FIG. 10 depicts the image as being redrawn to include a hatch pattern, it shall be understood that shading, grey scale or any other technique may be employed to amend how the selected color information is presented to the user. A black and white bitmap may be created, as well as a grayscale representation that uses for example 256 shades of gray, where each pixel of the grayscale image has a brightness value ranging from 0 (black) to 255 (white).

Hue Rotation as an Aid to Color Perception

Figure 12A:
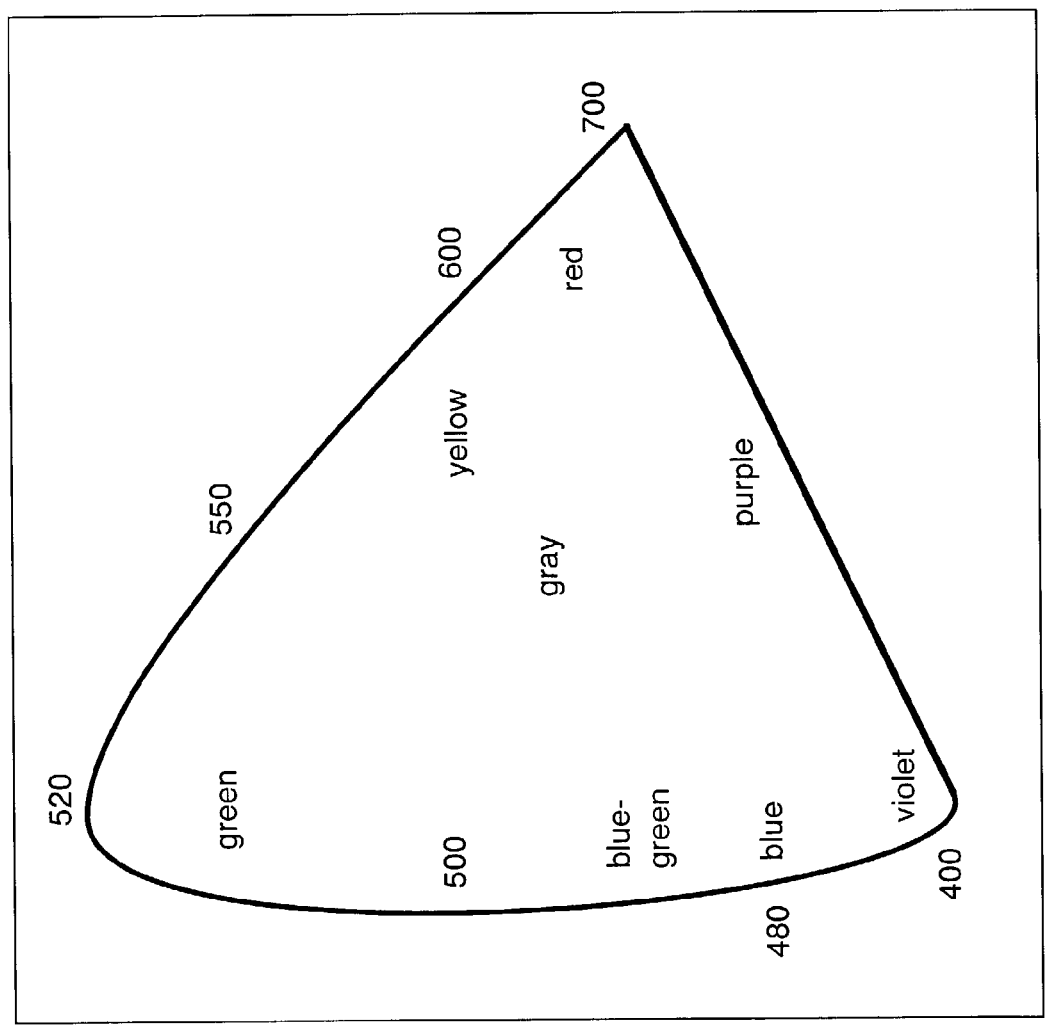
FIGS. 12A–12G depict a process for rotating a hue space from a first position to a second position.

FIG. 12A is a commonly understood diagram of normal color space: the C.I.E. chromaticity diagram (1931). In this representation, there is only hue and saturation shown, not lightness/darkness (value). In this respect, it is similar to the a circular hue plane in the HSL color space as well as to the rectangular AB plane in the LAB color space. A normally sighted person can differentiate between all the colors represented in this diagram.

Figure 12C:
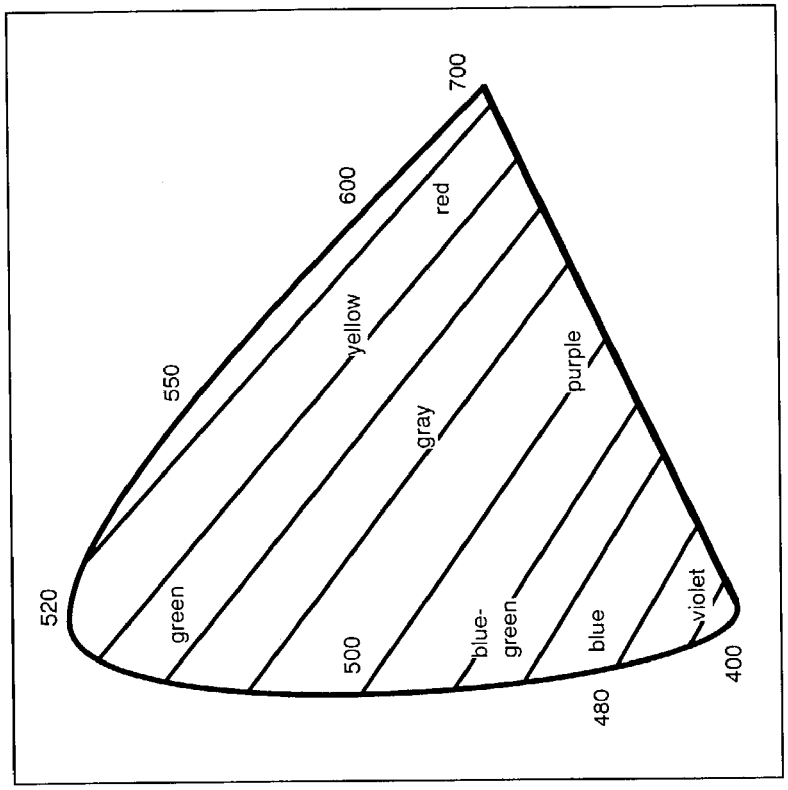
Figure 12B:
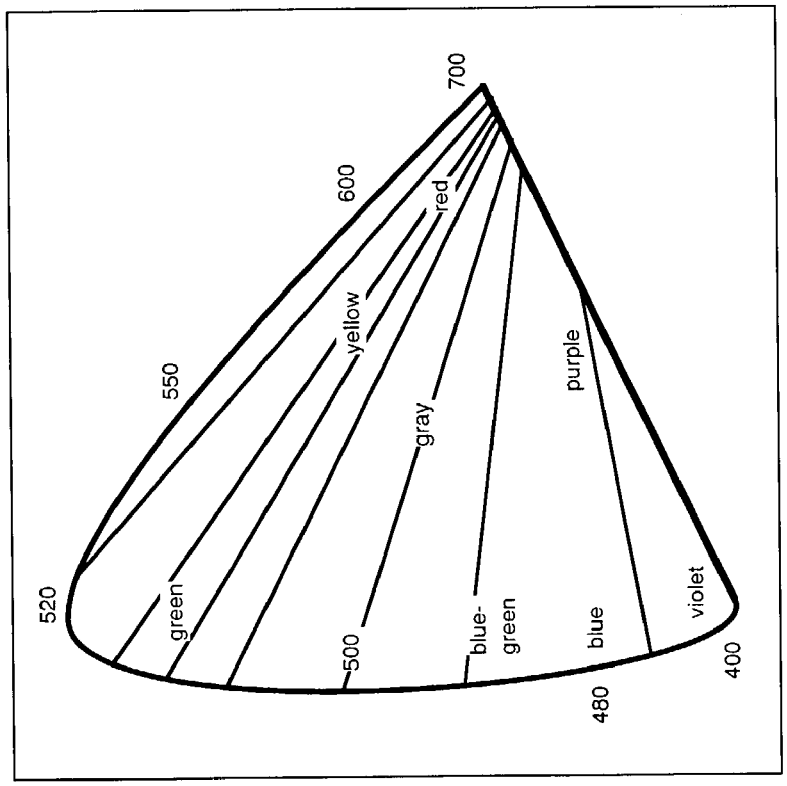
Figure 12D:
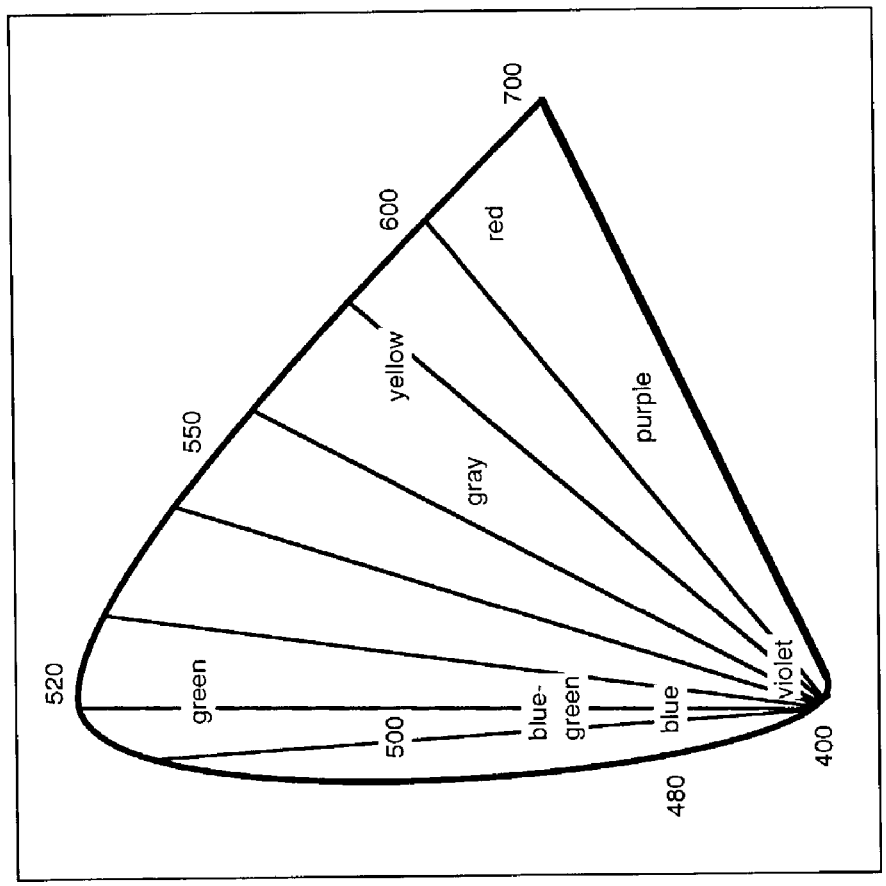

In terms of this color space representation, as shown in FIGS. 12B, 12C, and 12D, for different color blind persons there are different lines of "color confusion" or "isochromatic lines." Colors that lie on one of these lines or vectors cannot be differentiated one from another. Different forms of color blindness have different lines or vectors of color confusion. FIG. 12b represents one form of protanopia, FIG. 12C represents one form of deutanopia, FIG. 12D represents one form of tritanopia.

According to the literature, there seems to be not just a few, but rather many variations in these lines or vectors of color confusion among color blind people. It is difficult or impossible to choose one or even a few solutions for color display modifications that will work for all color blind people, even those nominally of the same type.

In a computer with a color display, a computer program will call for colors defined typically in an RGB color space to be displayed on a monitor, which again, typically, requires R, G, and B values. In a device in accordance with the invention, an intermediary color space is interposed on which the colors called for by the computer's program are mapped. This intermediary color space may be an RGB space, a CIE space, an HSL space, an LAB space, a CMYK space, a pseudo color space in which different colors are represented by different hatching patterns, or any other color space. The colors of this intermediate color space are in turn remapped onto the RGB values utilized by the display or printer output.

It can be seen that if the intermediate color space and the display color space are rotated in relation to each other, then when the computer program calls for a certain specific color to be output on the computer's display, another specific color will be displayed. Rotating these color spaces in relation to each other will thus re-map the input colors onto another set of colors.

For a color blind user, if there are two colors that both lie on one line or vector of color confusion, then rotating the intermediate color space may well result in two different colors that now do not lie on the same vector of color confusion and thus can now be successfully differentiated one from another.

What this means is that if there are two objects that are displayed on a computer monitor and the colors that render these two objects are such that a certain color blind person cannot tell them apart, then rotating the intermediate color space in relation to the display color space may now make the two objects look different (i.e. able to be differentiated from each other) to the color blind person. Because there are so many different forms of color blindness, giving the computer user the ability to rotate the color spaces him or herself will give the computer user the ability to find the exact setting that lets them do the best job of differentiating between the colors in each computer image or window in question.

When trying to differentiate between different color areas in a complex or subtle image on a computer display, even a normally-sighted person might find the invention useful.

Figure 12E:
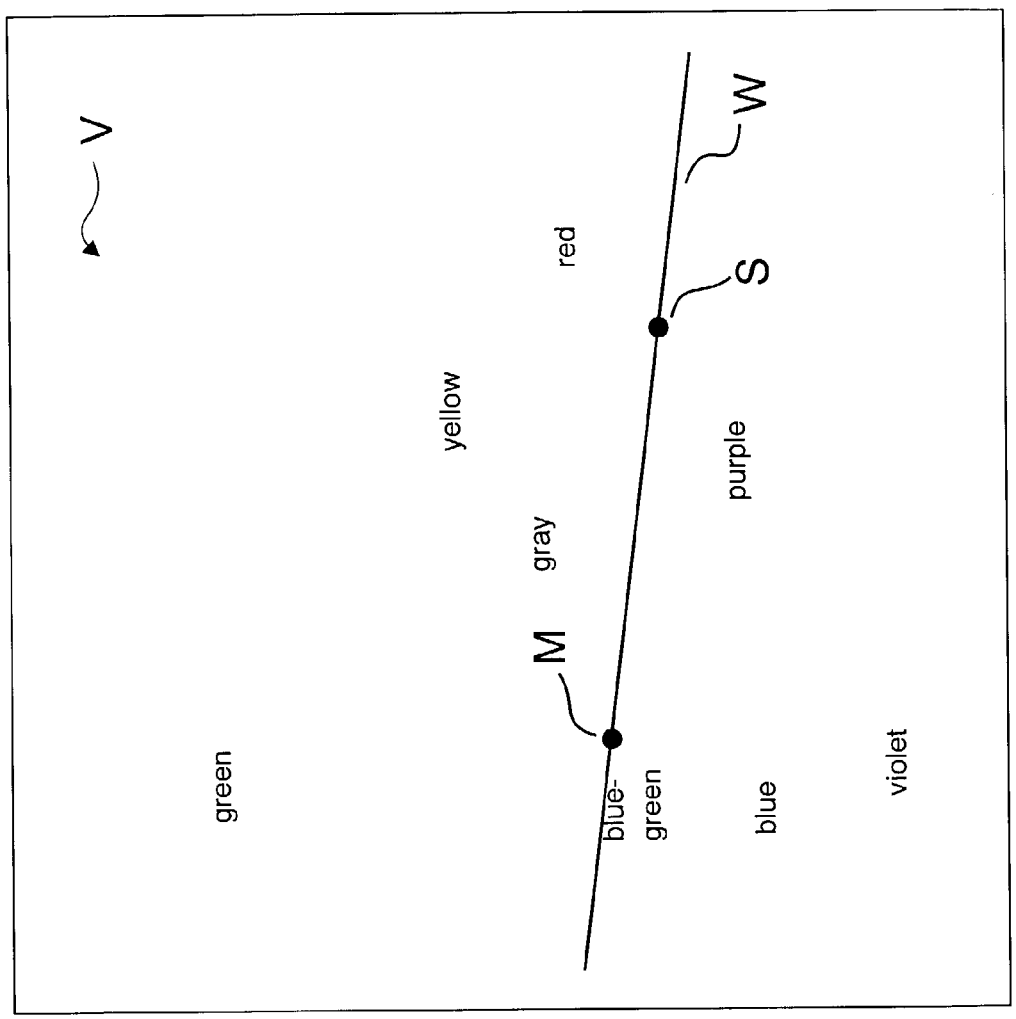

Accordingly, in alternative embodiments, the systems and methods described herein employ a color space rotation process to remap color-coded information from one portion of the color space to another portion of the color space. As shown in FIG. 12e, in an intermediate color space V, there are two colors M and S that a computer program is causing to be displayed on the computer monitor. Color M is blue-green hue and color S is a reddish-purple hue. These two hues both lie on a vector W of color confusion of a certain color blind person. Therefore, on the computer monitor, the hues of these two colors M and S look the same to the color blind person.

Figure 12F:
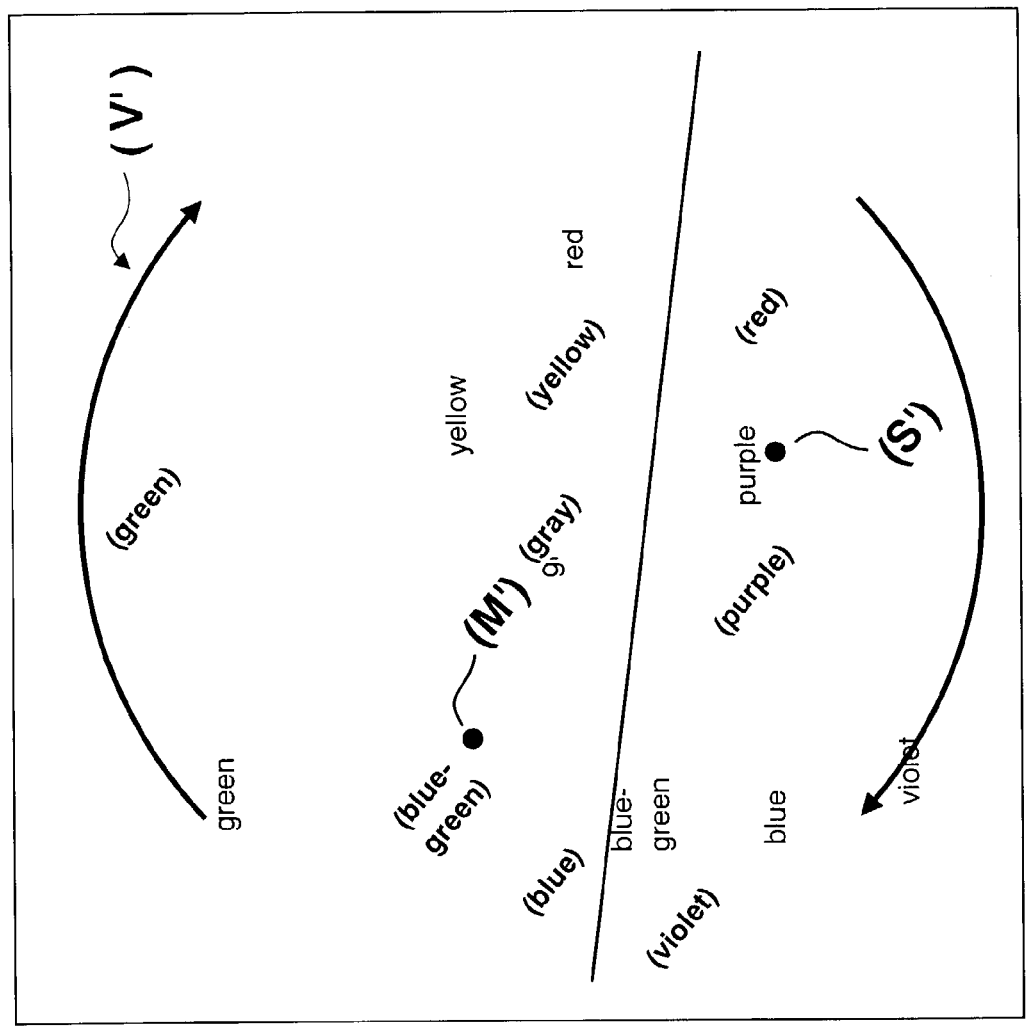

As shown in FIG. 12F, if using a device according to the invention the color blind person rotates the hues of the intermediate color space V to a new orientation V', then hues are remapped such that the two colors actually displayed on the computer's monitor have hues and M' and S'.

Figure 12G:
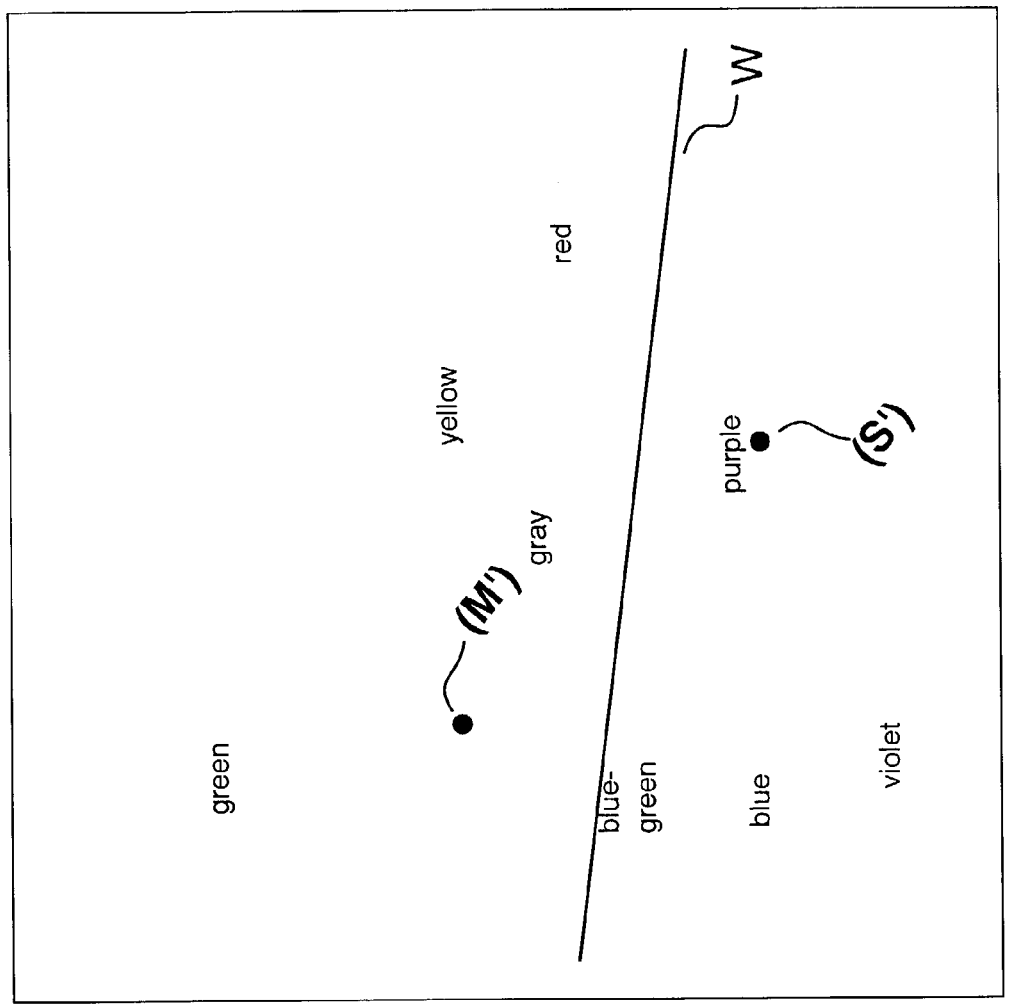

As show in FIG. 12G, with this remapping, M' will be displayed as a "yellower" green and S' will be displayed as a "bluer" purple. Note that these two hues do not lie on the color blind person's vector of confusion W. This means that the person will now be able to successfully discriminate between the two colors.

Thus, the systems and methods described herein can rotate the color space so that colors used to express information in an image are moved off a line of confusion for the user. This process moves colors into the perceptual space of the user. In optional embodiments the system can remap colors on the line of confusion to different locations that are off the confusion lines. This can be done by rotating the line or by substitution of colors on the line W, for colors that are not on the line W. In this practice, the system can identify colors in a color space that are absent form the image and which are not on the line W may be substituted for colors on the line W. In this way colors on the line W used to present information may be moved off the line and re-mapped to a color in the perceptual space of the user and not currently being used in the image.

Figure 13:
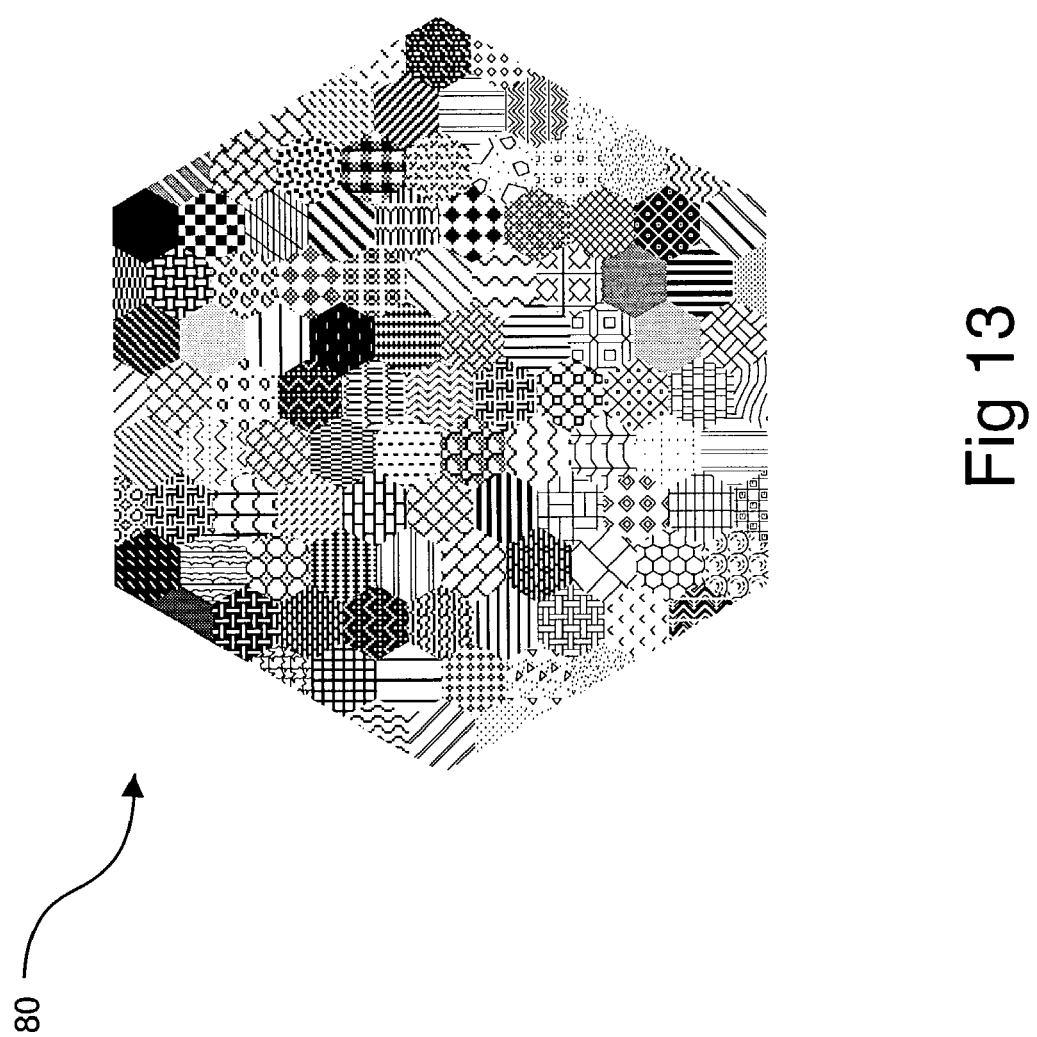
FIG. 13 depicts a pseudo color space comprising a plurality of hatching patterns.

As discussed above, FIG. 13 depicts a color space that is a pseudo color space 80 where different colors are represented by different hatching patterns. Color space 80 may act as the intermediate color space described above. In this case, a pixel color value in the original color space called for by the program can be mapped to a region in color space 80 that has a respective hatch pattern. Thus, in this embodiment a selected range of colors from the first color space are mapped to a specific region of this intermediate color space 80. This selected range of colors are identified as a contiguous area or areas as appropriate in the original image and filled with the respective hatching pattern associated with that selected range of colors. In this way the output presented to the user either on the display or in printer output—including a black and white printer's output—can more clearly differentiate between different color-coded data. Thus, the color space 80 may be a perceptual space for the user, and colors may be mapped to this perceptual space.

Figure 14:
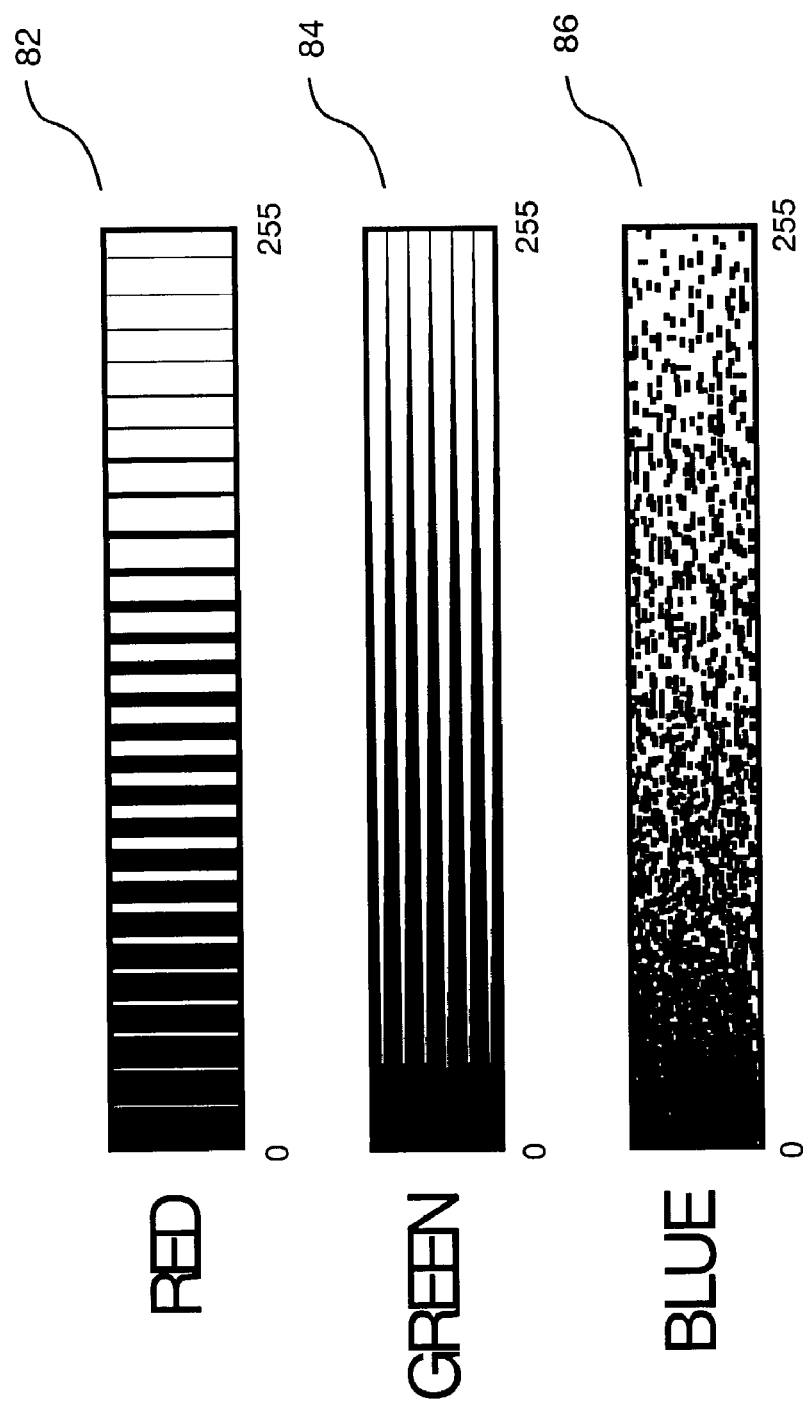
FIG. 14 depicts a plurality of color components assigned to respective hatching patterns.

In an alternate practice, color information can be mapped into a composite hatching pattern by assigning each component of the color, such as red green and blue, its own hatching pattern. For example, FIG. 14 depicts the three color components of an RGB defined color space. Figure three further shows that each of the components is assigned its own hatching pattern. For example color component red is assigned the hatching pattern 82. As shown, the hatching pattern 82 comprises a set of vertical lines where the line density decreases as the red value increases from 0 to 255. Thus a red color component having a know value such as 100 can be associated with a specific line density. Similar hatching patterns have been assigned to the green 84 and blue 86 components.

Figure 15:
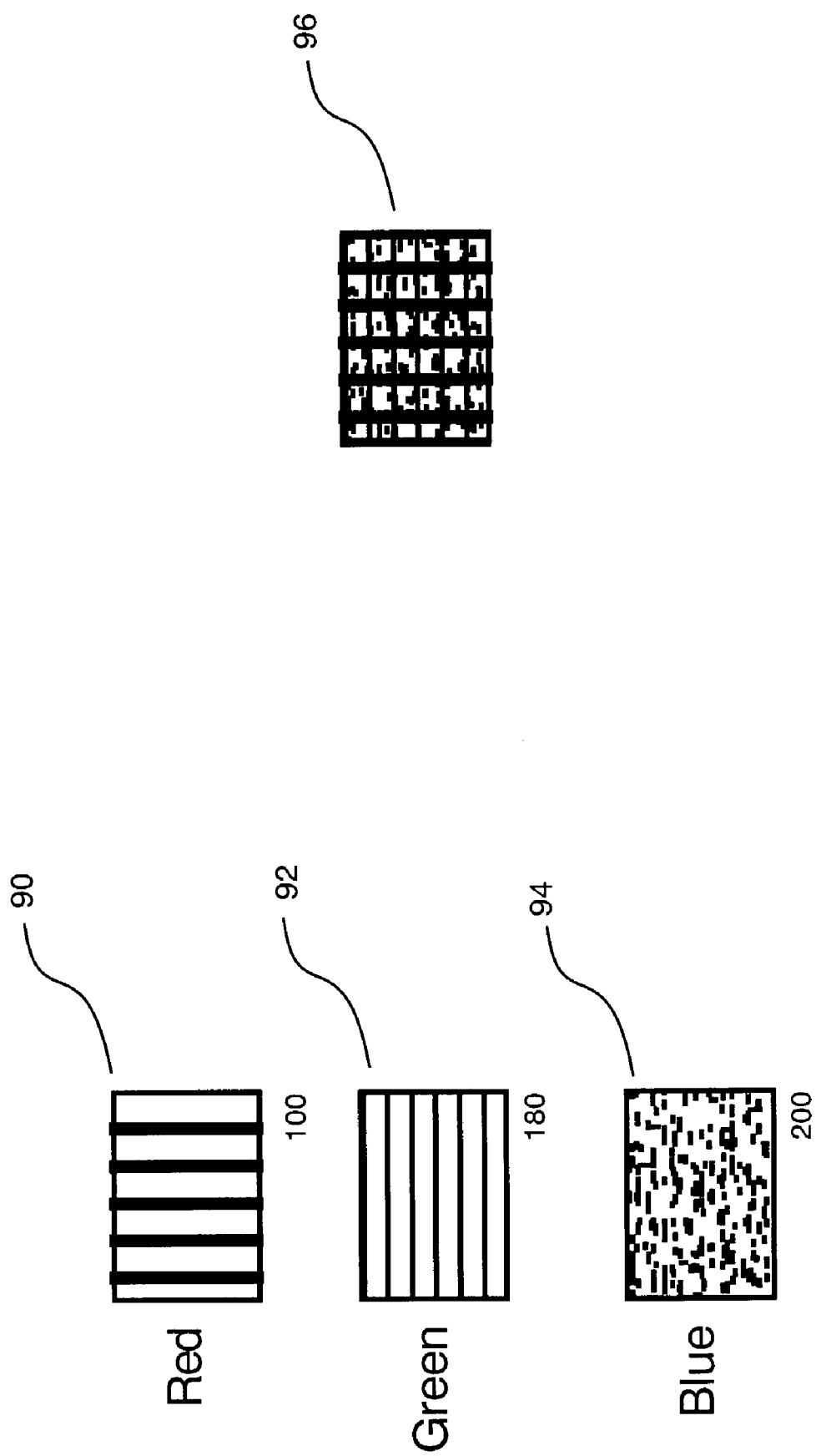
FIG. 15 depicts a process for superimposing hatching patterns to create a unique composite hatch pattern.

As shown in FIG. 15 a light greenish blue color which is defined in an RGB color space as having component values of R-100, G-180 and B-200 are assigned their associated hatching pattern. When these three hatching patterns are superimposed one on the other, a unique combined pattern will be created on the display or output. For example FIG. 15 depicts a composite pattern 96 formed from the superimposition of the patterns 90, 92 and 94. In other color spaces, there may be more or less than three associated hatching patterns. For example, a CMYK color space would have four hatching patterns, one pattern for each component of the CMYK color space.

Figure 17:
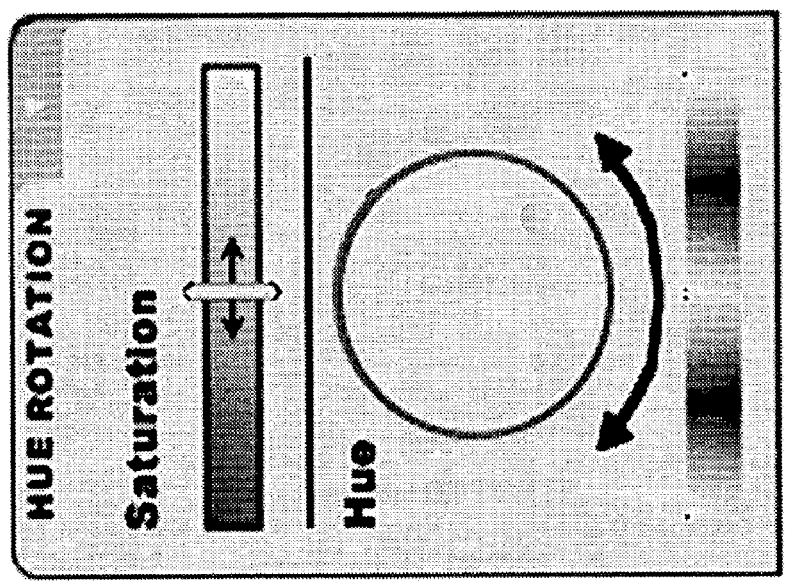
FIG. 17 depicts a GUI tool for achieving hue rotation.

One user interface that would be helpful would be a representation of a wheel or disk that is turned to rotate the intermediate color space and output color space in relation to each other. The wheel or disk that is turned to rotate the two hue maps in relation with each other. One such wheel is depicted in FIG. 17. There could also be a representation of a slider for the user to use in adjusting the saturation of the image. Especially if this control were configured such that increasing or decreasing the saturation of a image were to effect preferentially the areas of the image that have a color tone (as opposed to being essentially neutral or gray), the feature would further help the user in refining the color manipulation so as to better discern differences between different colored areas.

The systems described herein may employ the operating system API to control the display of colors on the computer display. Generally, an API provides a set of mathematical functions, commands and routines that are used when an application requests the execution of a low-level service that is provided by an OS. APIs differ depending on the OS types involved. A video system is employed to handle the output provided for a display unit. By applying VGA, SVGA or other appropriate standards, a video system determines how data is to be displayed and then converts digital signals of display data into analog signals to transmit to a display unit. It also determines what the refresh rate and standards of a dedicated graphics processor and then converts character and color data, received from an API as digital signals of display data, into analog signals that is thereafter transmitted to a display unit. As a result, predetermined characteristics are displayed on a screen.

A video system has two general display modes: a graphics mode and a text mode. The invention may be practiced in either mode. The graphics mode, however, is today the most important mode, and in this mode, data that are written in a video memory for display on a screen are handled as dot data. For example, for a graphics mode that is used to display 16 colors, in the video memory one dot on the screen is represented by four bits. Furthermore, an assembly of color data, which collectively is called a color palette, is used to represent colors, the qualities of which, when displayed on a screen, are determined by their red (R), green (G) and blue (B) element contents. Generally, in an eight bit mode, when the color combination represented by (R, G, B)=(255, 255, 255) is used, a white dot appears on the screen. Whereas, to display a black dot on a screen, a color combination represented by (R, G, B)=(0, 0, 0) is employed (hereinafter, unless otherwise specifically defined, the color elements are represented as (R, G, B)). An OS reads the color data designated by the color pallet and the character data (character code, characters and pictures uniquely defined by a user, sign characters, special characters, symbol codes, etc.), and on a screen displays characters using predetermined colors.

In one embodiment, this process described above is implemented as a software driver that processes the RGB data and drives the video display. In one embodiment, the software driver also monitors the position of the cursor as the cursor moves across the display. The driver detects the location of the cursor. If the cursor is over a portion of the screen that includes a color table, the software process determines the color under the cursor. To this end, the driver can determine the location of the cursor and the RGB value of the video data "under" the cursor. Thus the color that the cursor is "selecting" can be determined. The driver then processes the display in a manner such that any other pixel on that display having a color (RGB value) that is identical to the color, or some in cases substantially identical or within a selected range, is reprocessed to another color (black, white, or greys) in the color map. This results in an alternate image on the display. By having the driver reprocess the color in a way that is more perceptible to a color blind person, the color coded information in the image can be made more apparent to the color blind user. This is shown in FIG. 11 wherein the cursor is depicted over a portion of the key table and the portion of the pie chart having the same color as that portion of the key table is processed to change brightness over time. In this way a colorblind person can operate a mouse to relate the different sections of the pie charts to the key table and the information that section of the pie chart is intended to represent. At described above the system may be implemented as a video driver process. However, in alternate embodiments the system may be implemented as part of the operating system, as part of the application program, or as a plug-in, such as a plug-in that can execute with the Internet Explorer web browser. It would be understood that the systems and methods designed herein can be adapted to run on embedded systems including cell phone, PDAs, color displays of CNC or other industrial machines, game consoles, settop boxes, HDTV sets, lab equipment, digital cameras, and devices. In certain embodiments, the systems and methods described herein can alter the entire display, however, in other embodiments, such as those that work with a windows based display systems, such as X windows, only the active window will be effected, and optionally, each window may be effected and altered independently.

Changing of Color of Background-Non-Selected Colors to Another Color Code

The manner in which the RGB values are processed can vary according to the application, and optionally may be user selectable. For example, in one embodiment, the driver may process the image to cause colors other than the selected range to turn more gray. Optionally, those portions of the image that are not presented in the selected color may be presented in a black and white image. In a further optional embodiment, the system may alter the saturation of the display, such that portions of the image that are not presented in the selected color will fade to become less saturated. In a further practice, the system allows the user to lighten or darken the grayed out portions of the image and/or alter the contrast of the grayed out portion of the image.

Figure 16:
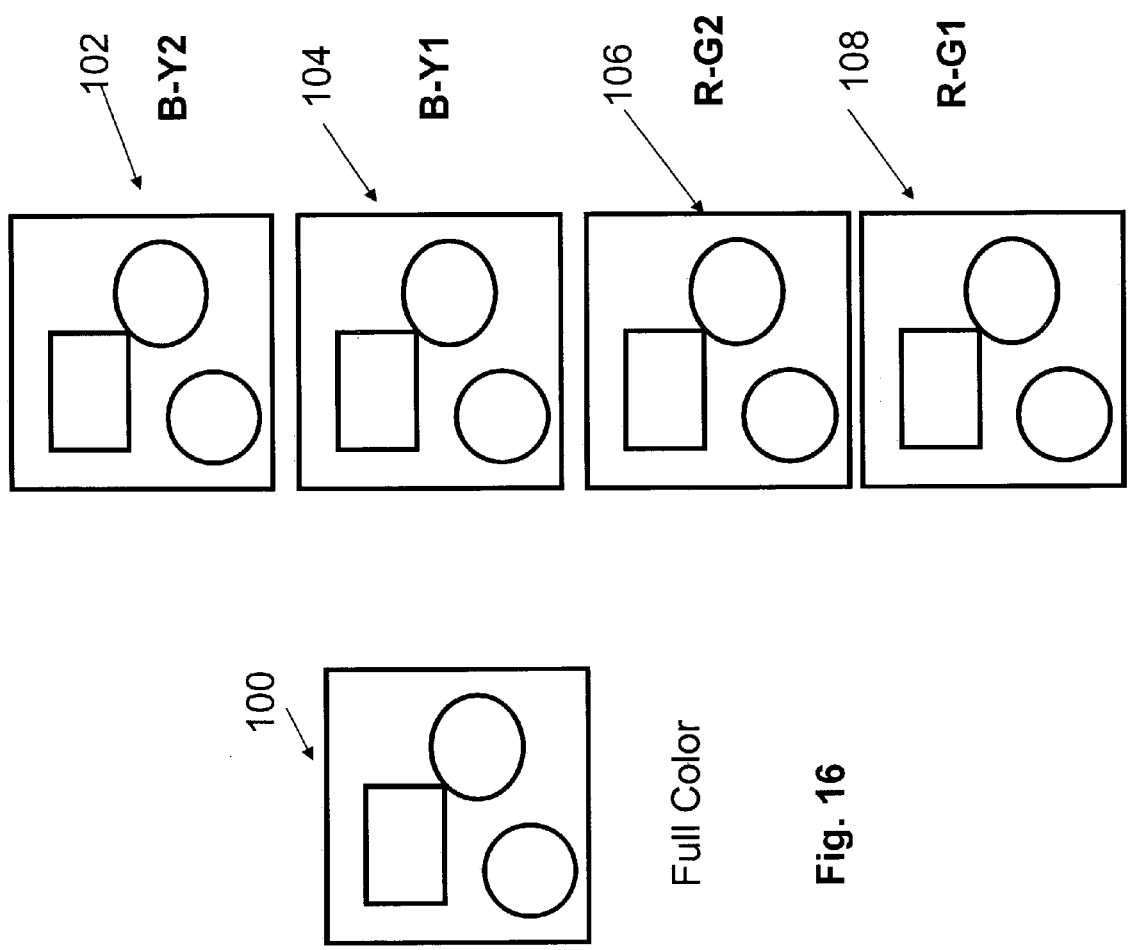
FIG. 16 depicts a process for allowing a user to identify a type of color blindness to consider when processing an image.

In a further embodiment, the systems and methods described herein may began with an initiation test that allows a color blind user to identify to the system the type of color blindness that the user has. To this end, and as depicted in FIG. 16, a display is presented to the user. On the display is a full color image 100 and a plurality of images 102, 104, 106 and 108 each of which presents a processed version of the full color image. These processed versions of the full color image are made by reducing a full color image from a three color space to a two color space and correspond to different types of color blindness. For example, the first image may present a particular kind of red and green color blindness, shown as RG1, and another image may present a different kind of red and green color blindness, shown as RG2, or as a version of blue and yellow (BY) color blindness. In either case the multiple images may be presented to the user and the user is allowed to select which of the images most closely matches the appearance of the full color image to the user. Once this information is provided to the system, the system may select the algorithm for processing the red, green and blue color values associated with the image being displayed to the user.

The user may also have control over how the image is represented, such as what and how many colors are processed, whether the processed colors are shown as getting darker or lighter, whether the colors flash or transition slowly, whether the colors are represented as having texture, like a hatch pattern, and other user controls. The application program can be PowerPoint, a web browser that uses color to show changes in the activation-status of hyperlinks, map displays, or some other program.

In a further alternative, the systems and methods described herein provide for treating color blindness. To this end, the systems and methods described herein include, in one embodiment, a computer game that may be played by males between the ages of six and fifteen. The computer game presents a series of images to the player. The player is asked to distinguish between different images and makes decisions based on his perception of these images. In this example game, the player is presented with two objects colored with two colors that the color blind person has difficulty in distinguishing. The player is rewarded for quickly tagging, in this example, the red object. However the player is penalized for tagging the wrong color object, in this case green. After a certain short time delay, the red, preferred target is identified to the player by overlaying a black texture that does not change the underlying color. The player can then tag the correct object for a lower score. In this way, the color blind player is encouraged to closely observe two colors he normally has difficulty in distinguishing and then have one color identified. Over time, as data is collected on the player, the game can be modified to make differentiation more challenging, such as by employing more subtle colors or presenting only one object at a time. By this game, the color blind player is given the tools to improve his ability to distinguish colors.

Although not to be limited by theory, it is a realization of the inventors that at least a portion color blindness arises from a central nervous system failure to allow a user to distinguish between different colors. Accordingly, the systems and methods described herein require the user to train their CNS system to detect a broader range of colors.

The systems and methods discussed above may be realized as a software component operating on a conventional data processing system such as a Windows, Apple or Unix workstation. In that embodiment, these mechanisms can be implemented as a C language computer program, or a computer program written in any high level language including C++, Fortran, Java or basic. Additionally, in an embodiment where microcontrollers or DSPs are employed, these systems and methods may be realized as a computer program written in microcode or written in a high level language and compiled down to microcode that can be executed on the platform employed. The development of such image processing systems is known to those of skill in the art, and such techniques are set forth in Digital Signal Processing Applications with the TMS320 Family, Volumes I, II, and III, Texas Instruments (1990). Additionally, general techniques for high level programming are known, and set forth in, for example, Stephen G. Kochan, *Programming in C*, Hayden Publishing (1983). It is noted that DSPs are particularly suited for implementing signal processing functions, including preprocessing functions such as image enhancement through adjustments in contrast, edge definition and brightness. Developing code for the DSP and microcontroller systems follows from principles well known in the art.

Those skilled in the art will know or be able to ascertain using no more than routine experimentation, many equivalents to the embodiments and practices described herein. Accordingly, it will be understood that the invention is not to be limited to the embodiments disclosed herein, but is to be understood from the following claims, which are to be interpreted as broadly as allowed under the law.

We claim:

1. A method for processing color image data for a user, comprising the steps of
    identifying a full color space defined by all colors associated with the color image data,
    identifying a first portion of the full color space,
    identifying a perceptual color space for the user, and
    by processing the color image data, mapping the first portion of the full color space to a portion of a perceptual space of the user,
    whereby, processing includes:
    selecting a color in the full color space; and
    at least one of displaying the selected color as a hatched pattern and flashing the selected color at a fundamental frequency wherein the flashing is perceptible to sighted people, and wherein the hatching pattern or flashing frequency is selected as a function of the selected color.

2. A method according to claim 1, including the further step of
    providing a user control for allowing the user to select at least one of adding a hatched pattern to the selected color and flashing the selected color at a fundamental frequency that is perceptible to sighted people.

3. A method according to claim 1, wherein selecting the color comprises selecting a color name from a list of color names, placing a cursor over a color in an image, or placing a cursor over a color in a key table.

4. A method according to claim 1, including the further step of providing a user control for selecting the perceptual space.

5. A method according to claim 4, wherein selecting the perceptual space includes selecting at least one of a set of different hatching patterns, a set of grey scale shades, a set of textures, and a set of flashing fundamental frequencies that are perceptible to sighted people, to render perceptible a corresponding set of at least one ambiguous color component located outside the perceptual color space, thereby identifying the at least one ambiguous color component for the user.

6. A method according to claim 4, wherein selecting the perceptual space includes assigning a hatching pattern to an ambiguous color component located outside the perceptual color space, to enable the user to identify the ambiguous color component.

7. A method according to claim 6, wherein the assigned hatching pattern is a scaled pattern that varies in respect to at least one of a magnitude of the ambiguous color component and location of the ambiguous color component relative to the perceptual space.

8. A method according to claim 6, including the further step of superimposing component hatching patterns corresponding to ambiguous color components to generate a hatching pattern representing the color image data.

9. A method according to claim 1, including the further step of identifying a second color space representative of a set of colors absent from the color image data and within the perceptual color space for the user.

10. A method according to claim 1, including the further step of allowing the user to rotate the full color space in relation to an alternate color space.

11. A method according to claim 10, including the further step of allowing the user to designate the alternate color space for displaying subsequent color images.

12. A method according to claim 10, wherein allowing the user includes providing a user control representative of a rotation wheel for rotating the full color space.

13. A method according to claim 1, wherein the full color space comprises a color space selected from the group consisting of LAB color space, HSL color space, and CMYK color space.

14. A method according to claim 1, wherein the color space comprises a three dimensional space defined as the red, green, blue color space.

15. A method according to claim 1, wherein identifying the first portion of the full color space includes identifying a portion of the color space having hues containing red or green.

16. A method according to claim 1, wherein identifying the first portion of the full color space includes identifying a portion of the color space having hues containing blue or yellow.

17. A method according to claim 1, wherein the processing further includes determining a lightness or darkness value present in the selected color.

18. A method according to claim 17, further including flashing the selected color at a frequency based on the lightness or darkness value of the selected color.

19. A method according to claim 17, further including allowing the user to determine lightness or darkness of the flashing of the selected color.

20. A method according to claim 1, wherein the processing includes selecting a color in the full color space and determining as a function of the blue or yellow hue present in the selected color a lightness or darkness value representative of an amount of blue or yellow hue present in the selected color.

21. A method according to claim 20, further including flashing the selected color based on the amount of blue or yellow hue present in the selected color.

22. A method according to claim 1, wherein the first portion of the full color space includes a line of color confusion having color components indistinguishable by the user.

23. A method according to claim 22, wherein the mapping includes translating ambiguous color image data, located on the line of confusion, to a location in a color space off the line of confusion.

24. A method according to claim 23, wherein the translating includes rotating at least a portion of the full color space.

25. A method for processing color image data to be presented on a computer display to a user, comprising:
    identifying a full color space defined by all colors associated with the color image data,
    allowing the user to map a first portion of the full color space into a portion of a perceptual space of the user, and
    modifying video image data associated with the color image data as a function of the translated color space,
    wherein the first portion of the full color space includes a line of color confusion having color components indistinguishable by the user, and
    whereby mapping includes selecting ambiguous color image data located on the line of confusion, and at least one of displaying the selected color image data as a hatched pattern and flashing the selected color image data at a fundamental frequency, wherein the flashing is perceptible to sighted people, and wherein the hatching pattern or flashing frequency is selected as a function of the selected color.

26. A video driver capable of processing color image data to be presented on a color display to a user, comprising:
    a data memory having stored therein a full color space defined by all colors associated with the data, and data representative of a first portion of the color space having at least one pair of colors indistinguishable to the user,
    means for modifying video image data associated with the first portion by at least one of hatching a selected color from the first portion and flashing a selected color from the first portion at a fundamental frequency wherein the flashing is perceptible to sighted people, and wherein the hatching pattern or flashing frequency is selected as a function of the selected color.

27. A video driver according to claim 26, further comprising means for identifying portions of the color space having colors that are absent from the image data.

* * * * *